(12) United States Patent
Lee et al.

(10) Patent No.: US 8,148,137 B2
(45) Date of Patent: Apr. 3, 2012

(54) MUTANT MICROORGANISM HAVING IMPROVED PRODUCTION ABILITY OF BRANCHED AMINO ACID AND METHOD FOR PREPARING BRANCHED AMINO ACID USING THE SAME

(75) Inventors: Sang Yup Lee, Yuseong-gu (KR); Jin Hwan Park, Yeongtong-gu (KR); Kwang Ho Lee, Yuseong-gu (KR); Tae Yong Kim, Yong In-si (KR)

(73) Assignee: Korea Advanced Institute of Science & Technology, Daejeon (KR)

( * ) Notice: Subject to any disclaimer, the term of this patent is extended or adjusted under 35 U.S.C. 154(b) by 765 days.

(21) Appl. No.: 12/097,099

(22) PCT Filed: Mar. 14, 2007

(86) PCT No.: PCT/KR2007/001263
§ 371 (c)(1),
(2), (4) Date: Jun. 12, 2008

(87) PCT Pub. No.: WO2008/088104
PCT Pub. Date: Jul. 24, 2008

(65) Prior Publication Data
US 2009/0053779 A1    Feb. 26, 2009

(30) Foreign Application Priority Data
Jan. 17, 2007 (KR) .................. 10-2007-0005268

(51) Int. Cl.
*C12N 1/21* (2006.01)
*C12P 13/08* (2006.01)

(52) U.S. Cl. ................. 435/252.33; 435/115
(58) Field of Classification Search ................. None
See application file for complete search history.

(56) References Cited

U.S. PATENT DOCUMENTS

| | | | |
|---|---|---|---|
| 5,888,783 A | 3/1999 | Tomita et al. | |
| 6,737,255 B2 | 5/2004 | Livshits et al. | |
| 6,841,360 B2 | 1/2005 | Kennerknecht et al. | |
| 7,632,663 B1 * | 12/2009 | Eggeling et al. ............ | 435/106 |
| 2005/0239175 A1 | 10/2005 | Tabolina et al. | |

FOREIGN PATENT DOCUMENTS

| WO | WO 00/50624 | 8/2000 |
|---|---|---|
| WO | WO 2006/107127 A1 | 10/2006 |

OTHER PUBLICATIONS

Veronika Elišáková et al., "Feedback-Resistant Acetohydroxy Acid Synthase Increases Valine Production in *Corynebacterium glutamicum*" Applied and Environmental Microbiology, Jan. 2005, vol. 71, No. 1, p. 207-213.
Nicole Kennerknecht et al., "Export of L-Isoleucine from *Corynebacterium glutamicum*: a Two-Gene-Encoded Member of a New Translocator Family" Journal of Bacteriology, Jul. 2002, vol. 184, No. 14, p. 3947-3956.
Steven A. Haney et al., "Lrp, a Leucine-Responsive Protein, Regulates Branched-Chain Amino Acid Transport Genes in *Escherichia coli*" Journal of Bacteriology, Jan. 1992, vol. 174, No. 1, p. 108-115.
Jill V. Platko et al., "The ilvIH Operon of *Escherichia coli* Is Positively Regulated" Journal of Bacteriology, Aug. 1990, vol. 172, No. 8, p. 4563-4570.
Lee et al., "MetaFluxNet: the management of metabolic reaction information and quantitative metabolic flux analysis," Bioinformatics (2003) 19 (16): 2144-2146.
Lee et al., "Batch and continuous cultures of *Mannheimia succiniciproducens* MBEL55E for the production of succinic acid from whey and corn steep liquor," Bioprocess Biosyst. Eng. (2003) 26: 63-67.
Segrè et al., "Analysis of optimality in natural and perturbed metabolic networks," *PNAS* (2002) 99 (23): 15112-15117.
Datsenko et al., "One-step inactivation of chromosomal genes in *Escherichia coli* K-12 using PCR products," *PNAS* (2000) 97 (12): 6640-6645.
Jäger et al., "Expression of the *Bacillus subtilis* sacB gene leads to sucrose sensitivity in the gram-positive bacterium *Corynebacterium glutamicum* but not in *Streptomyces lividans*," *J. Bacteriology* (1992) 174 (16): 5462-5465.
Jafri et al., "*ilvIH* operon expression in *Escherichia coli* requires Lrp binding to two distinct regions of DNA," *J. Bacteriology* (2002) 184 (19): 5293-5300.
Radmacher et al., "Linking central metabolism with increase pathway flux: L-Valine accumulation by *Corynebacterium glutamicum*," *Applied Environmental and Microbiology* (2002) 68(5): 2246-2250.
Daldal et al., "Molecular cloning of the gene for phosphofructokinase-2 of *Escherichia coli* and the Nature of a mutation, *pfk*B1, causing a high level of the enzyme," *J. Mol. Biol.* (1983) 168: 285-305.
Lee et al., "Batch and continuous cultivation of *Anaerobiospirillum succiniciproducens* for the production of succinic acid from whey," *Appl. Microbiol. Biotechnol.* (2000) 54: 23-27.
Lee et al., "Isolation and characterization of new succinic acid-producing bacterium, *Mannheimia succiniciproducens* MBEL55E, from bovine rumen," *Appl. Microbiol. Biotechnol.* (2002) 58: 663-668.
Lee et al., "Aerobic production of alanin by *Escherichia coli* aceF ldhA mutants expressing the *Bacillus sphaericus* alaD gene," *Appl. Microbiol. Biotechnol.* (2004) 65: 56-60.

(Continued)

*Primary Examiner* — Rebecca E. Prouty
(74) *Attorney, Agent, or Firm* — Merchant & Gould P.C.

(57) ABSTRACT

The present invention relates to mutant microorganisms having improved productivity of branched-chain amino acids, and a method for producing branched-chain amino acids using the mutant microorganisms. More specifically, relates to mutant microorganisms having improved productivity of L-valine, which are produced by attenuating or deleting a gene encoding an enzyme involved in L-isoleucine biosynthesis, a gene encoding an enzyme involved in L-leucine, and a gene encoding an enzyme involved in D-pantothenic acid biosynthesis, and mutating a gene encoding an enzyme involved in L-valine biosynthesis, such that the expression thereof is increased, as well as a method for producing L-valine using the mutant microorganisms. The inventive mutant microorganisms produced by site-specific mutagenesis and metabolic pathway engineering can produce branched-chain amino acids, particularly L-valine, with high efficiency, and thus will be useful as industrial microorganisms for producing L-valine.

2 Claims, 7 Drawing Sheets

OTHER PUBLICATIONS

Lee et al., "Succinic acid production with reduced by-product formation in the fermentation of *Anaerobiospirillum succiniciproducens* using glycerol as a carbon source," *Biotechnol. Bioeng.* (2001) 72: 41-48.

Lee et al, "Biological conversion of wood hydrolysate to succinic acid by *Anaerobiospirillum succiniciproducens*," *Biotechnology Letters* (2003) 25: 111-114.

International Search Report for corresponding PCT application PCT/KR2007/001263.

* cited by examiner

US 8,148,137 B2

MUTANT MICROORGANISM HAVING IMPROVED PRODUCTION ABILITY OF BRANCHED AMINO ACID AND METHOD FOR PREPARING BRANCHED AMINO ACID USING THE SAME

TECHNICAL FIELD

The present invention relates to mutant microorganisms having improved productivity of branched-chain amino acids, and a method for producing branched-chain amino acids using the mutant microorganisms, and more specifically to mutant microorganisms having improved productivity of L-valine, which are produced by attenuating or deleting a gene encoding an enzyme involved in L-isoleucine biosynthesis, a gene encoding an enzyme involved in L-leucine, and a gene encoding an enzyme involved in D-pantothenic acid biosynthesis, and mutating a gene encoding an enzyme involved in L-valine biosynthesis, such that the expression thereof is increased, as well as a method for producing L-valine using the mutant microorganisms.

BACKGROUND ART

These days, most amino acids are being produced using microorganisms, constructed by random mutagenesis techniques. These microbial strains have a shortcoming in that it is difficult to additionally improve the strains, because it is difficult to understand the precise physiological metabolism thereof. Thus, a rational design technique is required, in which only specific genes are deleted or amplified, such that desired amino acids are produced.

As used herein, the term "branched-chain amino acids" refers to three substances, valine, leucine and isoleucine, among nine essential amino acids. Unlike most other amino acids which are metabolized in the liver, the branched-chain amino acids are metabolized mainly in muscles, such that they are used as energy sources for moving the body.

Currently, the market share of the branched chain amino acids is only 1%, but is increasing fast, since it was recently reported that the branched chain amino acids play an important role in maintaining and building muscles for moving the body. In particular, L-valine has been used as a feed component, since it was reported that L-valine has high reducing power and serves to increase the ability of cows to produce milk. Although L-valine has generally been produced from bacterial strains, such as *Brevibacterium, Corynebacterium* or *Serratia* sp., it was recently reported that L-valine was produced in *E. coli* strains, which are easy to culture and allows the use of advanced molecular biological techniques. In particular, Ajinomoto Co., Inc., Japan, reported that a bacterial strain having resistance to L-valine was screened using a random mutagenesis technique and it produced 23.4 g/l of L-valine (U.S. Pat. No. 6,737,255).

Also, the production of L-valine-producing microorganisms (*Corynebacterium glutamicum*) using a rational design technique was recently reported, in which 130 mM of L-valine was produced using microorganisms, obtained by deleting two genes (ilvA and panB), amplifying an operon (ilvBNC) involved in L-valine biosynthesis, and then removing feedback inhibition of the ilvN gene (Veronika et al., *Appl. Environ. Microbiol.*, 71:207, 2005). However, an example, in which L-valine was produced in *E. coli* using the rational design method, has not been reported yet.

Among various rational design methods, in silico simulation methods, particularly analysis and prediction techniques using metabolic pathways, have recently shown its possibilities along with rapidly increasing genome information. In particular, by the combination of microbial metabolic pathway models with mathematical models and optimization techniques, it has become possible to predict reactions in metabolic pathways, which occur after the removal or addition of genes. Also, it is known that a technique of analyzing metabolic fluxes using metabolic pathways shows ideal cellular metabolic fluxes without requiring dynamic information and can substantially simulate and predict the precise behavior of cells. Metabolic flux analysis obtains an ideal metabolic flux space that cells can reach using only a set of metabolic mass balancing reactions and cell composition information, and it aims to maximize or minimize a specific objective function through an optimization method (either maximization of cell growth rate or minimization of metabolic regulation by specific perturbation). In addition, metabolic flux analysis can be used to analyze the lethality of a specific gene in a desired metabolite through bacterial strain improvement and to understand the characteristics of metabolic pathways in bacterial strains. Moreover, studies on the various applications of metabolic flux analysis for predicting the change in metabolic pathway flux, which is caused by the removal or addition of genes, have been reported.

Thus, in the art to which the present invention pertains, there is an urgent need to develop microorganisms having high productivity of branched-chain amino acids, particularly, *E. coli* strains having high productivity of L-valine, using the rational design method which comprises reconstructing metabolic pathways through the deletion of specific genes and amplifying desired genes, unlike the prior random mutagenesis techniques.

Accordingly, the present inventors have made many efforts to develop microorganisms having high productivity of branched-chain amino acids, particularly L-valine, using the rational design method. As a result, the present inventors have found that mutant microorganisms, produced by substituting a native promoter containing the attenuators of L-valine biosynthesis operons with a strong promoter, inserting an operon containing the substituted promoter into a recombinant vector, and then introducing the recombinant vector into *E. coli* having a deletion of ilvA, leuA and panB genes involved in competitive pathways, can produce L-valine with high productivity and efficiency, thereby completing the present invention.

SUMMARY OF THE INVENTION

Therefore, it is a main object of the present invention to provide mutant microorganisms having high productivity of L-valine, as well as a production method thereof.

Another object of the present invention is to provide a method for producing L-valine using said mutant microorganisms.

To achieve the above object, the present invention provides a method for producing mutant microorganisms having high productivity of L-valine, the method comprising attenuating or deleting a gene encoding an enzyme involved in L-isoleucine biosynthesis, a gene encoding an enzyme involved in L-leucine biosynthesis, and a gene encoding an enzyme involved in D-pantothenic acid biosynthesis, in microorganisms, and mutating a gene encoding an enzyme involved in L-valine biosynthesis, such that the expression thereof is increased.

The present invention also provides mutant microorganisms prepared by said method, in which a gene encoding an enzyme involved in L-isoleucine biosynthesis, a gene encoding an enzyme involved in L-leucine biosynthesis, and a gene encoding an enzyme involved in D-pantothenic acid biosynthesis, are attenuated or deleted, and a gene encoding an enzyme involved in L-valine biosynthesis is mutated such that the expression thereof is increased.

The present invention also provides a mutant microorganism having high productivity of L-valine, in which (a) ilvA, leuA and panB are attenuated or deleted; (b) an lacI gene is deleted; (c) feedback inhibition of an ilvH gene is removed; (d) a native promoter, containing the attenuators of ilvGMEDA and ilvBN operons, is substituted with a strong promoter; (e) an expression vector, containing ilvB, ilvN, ilvC, ilvE and ilvD genes and a strong promoter, is introduced; and (f) a branched-chain amino acid exporter of SEQ ID NO: 45 is amplified or introduced.

The present invention also provides a mutant microorganism having high productivity of L-valine, in which (a) ilvA, leuA and panB are attenuated or deleted; (b) an lacI gene is deleted; (c) feedback inhibition of an ilvH gene is removed; (d) a native promoter, containing the attenuators of ilvGMEDA and ilvBN operons, is substituted with a strong promoter; (e) an expression vector, containing ilvB, ilvN, ilvC, ilvE and ilvD and a strong promoter, is introduced; and (f) aceF and pfkA genes are attenuated or deleted.

The present invention also provides a mutant microorganism having high productivity of L-valine, in which (a) ilvA, leuA and panB are attenuated or deleted; (b) an lacI gene is deleted; (c) feedback inhibition of an ilvH gene is removed; (d) a native promoter, containing the attenuators of ilvGMEDA and ilvBN operons, is substituted with a strong promoter; (e) an expression vector, containing ilvB, ilvN, ilvC, ilvE and ilvD genes and a strong promoter, is introduced; and (f) aceF, pfkA and mdh genes are attenuated or deleted.

The present invention also provides a method for producing L-valine, the method comprising culturing said microorganisms having high productivity of L-valine; and then collecting L-valine from the culture broth of the microorganisms.

The above and other objects, features and embodiments of the present invention will be more clearly understood from the following detailed description and accompanying claims.

BRIEF DESCRIPTION OF THE DRAWINGS

In FIG. 5, "A" shows the relationship between cell growth rate and L-valine production rate, according to the deletion of the first gene, "B" shows the relationship between cell growth rate and L-valine production rate, according to the deletion of the second gene, and "C" shows the relationship between cell growth rate and L-valine production rate, according to the deletion of the third gene.

DETAILED DESCRIPTION OF THE INVENTION, AND PREFERRED EMBODIMENTS

Figure 1:
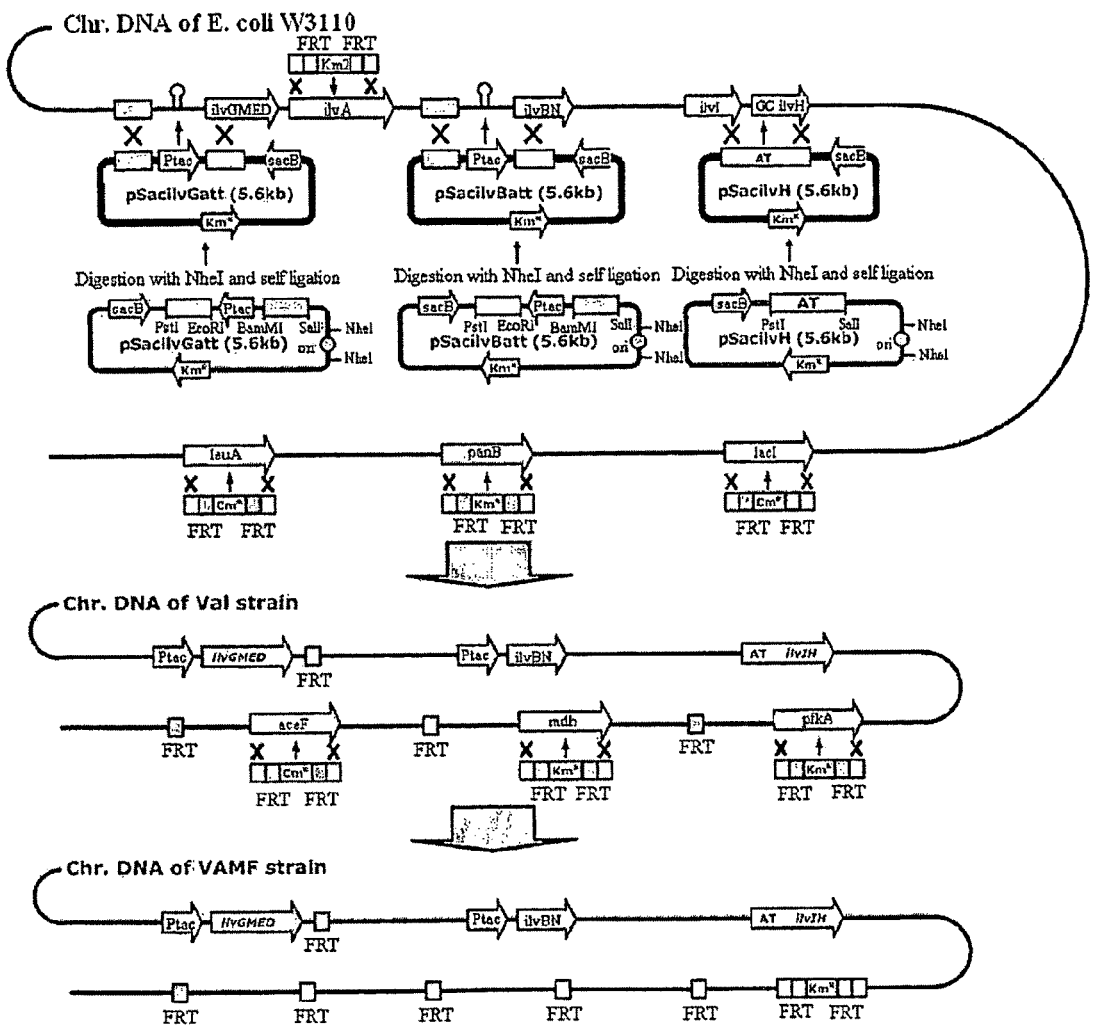
FIG. 1 shows a process of manipulating only the target gene in wild-type strain E. coli W3110 to produce L-valine-producing microorganisms and introducing a deletion of genes to be deleted into the produced microorganisms.

In one aspect, the present invention relates to a method for producing mutant microorganisms having high productivity of L-valine, the method comprising attenuating or deleting a gene encoding an enzyme involved in L-isoleucine biosynthesis, a gene encoding an enzyme involved in L-leucine biosynthesis, and a gene encoding an enzyme involved in D-pantothenic acid biosynthesis, in microorganisms, and mutating a gene encoding an enzyme involved in L-valine biosynthesis such that the expression thereof is increased.

In another aspect, the present invention relates to mutant microorganisms, in which a gene encoding an enzyme involved in L-isoleucine biosynthesis, a gene encoding an enzyme involved in L-leucine biosynthesis, and a gene encoding an enzyme involved in D-pantothenic acid biosynthesis, are attenuated or deleted, and a gene encoding an enzyme involved in L-valine biosynthesis is mutated such that the expression thereof is increased.

In the present invention, said microorganisms are preferably selected from the group consisting of bacteria, yeasts and fungi. Said bacteria are preferably selected from the group consisting of Corynebacterium sp., Brevibacterium sp., and E. coli. More preferably, the bacteria are E. coli.

In the present invention, the gene encoding an enzyme involved in L-isoleucine biosynthesis is preferably ilvA (gene encoding threonine dehydratase), the gene encoding an enzyme involved in L-leucine biosynthesis is preferably leuA (gene encoding 2-isopropylmalate synthase), and the gene encoding an enzyme involved in D-pantothenic acid biosynthesis is preferably panB (gene encoding 3-methyl-2-oxobutanoate hydroxymethyltransferase).

In the present invention, mutation of the gene encoding an enzyme involved in L-valine biosynthesis so as to increase the expression of the gene is preferably performed by any one selected from the group consisting of the followings: (a) deletion of lacI (gene encoding an lac operon repressor); (b) removal of feedback inhibition of an ilvH (acetohydroxy acid synthase isozyme III) gene; (c) substitution of a native promoter, containing the attenuators of ilvGMEDA (acetohydroxy acid synthase isozyme I) and ilvBN (acetohydroxy acid synthase isozyme II) operons, with a strong promoter; and (d) introduction of an expression vector containing the strong promoter.

In the present invention, the strong promoter is preferably selected from the group consisting of a trc promoter, a tac promoter, a T7 promoter, a lac promoter and a trp promoter. Also, the expression vector containing the strong promoter is preferably a vector containing ilvB, ilvN, ilvC, ilvE and ilvD genes. Moreover, the expression vector is preferably a pKBRilvBNCED vector.

The inventive method for producing mutant microorganisms may additionally comprise attenuating or deleting one or more genes selected from the group consisting of aceE, aceF, lpdA, pfkA, pfkB, tpiA, sdhA, sdhB, sdhC, sdhD, fumA, fumB, fumC, eptB, gpmA, gpmB, ptsG, mdh, ppc, pgi, glgC, sucA, sucB, ribA, folE and ackA. Preferably, the inventive method additionally comprises attenuating or deleting aceF and pfkA genes, and more preferably, the inventive method additionally comprises attenuating or deleting aceF, pfkA and mdh genes.

The inventive method may additionally comprise amplifying or introducing a branched-chain amino acid exporter gene. Preferably, the branched-chain amino acid exporter gene is at least one selected from the group consisting of base sequences encoding amino acid sequences of SEQ ID NO: 43 and SEQ ID NO: 44, or has a base sequence of SEQ ID NO: 45.

The inventive method may additionally comprise amplifying or introducing a global regulator lrp gene. The lrp gene preferably has a base sequence of SEQ ID NO: 46.

In another aspect, the present invention relates to a mutant microorganism having high productivity of L-valine, in which (a) ilvA, leuA and panB are attenuated or deleted; (b) an lacI gene is deleted; (c) feedback inhibition of an ilvH gene is removed; (d) a native promoter, containing the attenuators of ilvGMEDA and ilvBN operons, is substituted with a strong promoter; (e) an expression vector, containing ilvB, ilvN, ilvC, ilvE and ilvD genes and a strong promoter, is introduced; and (f) a branched-chain amino acid exporter of SEQ ID NO: 45 is amplified or introduced.

In the inventive mutant microorganism having high productivity of L-valine, an lrp gene of SEQ ID NO: 46 is preferably additionally amplified or introduced.

In still another aspect, the present invention relates to a mutant microorganism having high productivity of L-valine, in which (a) ilvA, leuA and panB are attenuated or deleted; (b) an lacI gene is deleted; (c) feedback inhibition of an ilvH gene is removed; (d) a native promoter, containing the attenuators of ilvGMEDA and ilvBN operons, is substituted with a strong promoter; (e) an expression vector, containing ilvB, ilvN, ilvC, ilvE and ilvD and a strong promoter, is introduced; and (f) aceF and pfkA genes are attenuated or deleted.

In the inventive mutant microorganism having high productivity of L-valine, a branched-chain amino acid exporter gene of SEQ ID NO: 45 is preferably additionally amplified or introduced. Also, an lrp gene of SEQ ID NO: 46 is preferably additionally amplified or introduced.

In still another aspect, the present invention relates to a mutant microorganism having high productivity of L-valine, in which (a) ilvA, leuA and panB are attenuated or deleted; (b) an lacI gene is deleted; (c) feedback inhibition of an ilvH gene is removed; (d) a native promoter, containing the attenuators of ilvGMEDA and ilvBN operons, is substituted with a strong promoter; (e) an expression vector, containing ilvB, ilvN, ilvC, ilvE and ilvD genes and a strong promoter, is introduced; and (f) aceF, pfkA and mdh genes are attenuated or deleted.

In the inventive mutant microorganism having high productivity of L-valine, a branched-chain amino acid exporter gene of SEQ ID NO: 45 is preferably additionally amplified or introduced. Also, an lrp gene of SEQ ID NO: 46 is preferably additionally amplified or introduced therein.

In yet another aspect, the present invention relates to a method for producing L-valine, the method comprising culturing said microorganisms having high productivity of L-valine; and then collecting L-valine from the culture broth of the microorganisms.

In the present invention, in order to produce a microorganism (Val) having high productivity of L-valine, as shown in FIG. 1, the activity of an enzyme involved in L-valine biosynthesis in wild-type strain E. coli W3110 is increased, and the activities of an enzyme involved in L-isoleucine biosynthesis, an enzyme involved in L-leucine biosynthesis and an enzyme involved in D-pantothenic acid biosynthesis in the E. coli strain are attenuated or deleted. That is, the microorganism (Val) is constructed by substituting a native promoter, containing the L-valine biosynthesis operon, with a strong promoter, and deleting ilvA, leuA and panB genes involved in pathways competitive with respect to the L-valine biosynthesis pathway.

Also, in order to improve the L-valine productivity of the constructed mutant microorganism, as shown in FIG. 1, aceF, mdh and pfkA are deleted from the E. coli mutant strain Val, thus constructing a mutant microorganism (VAMF) having an improved ability to produce L-valine.

Figure 2:
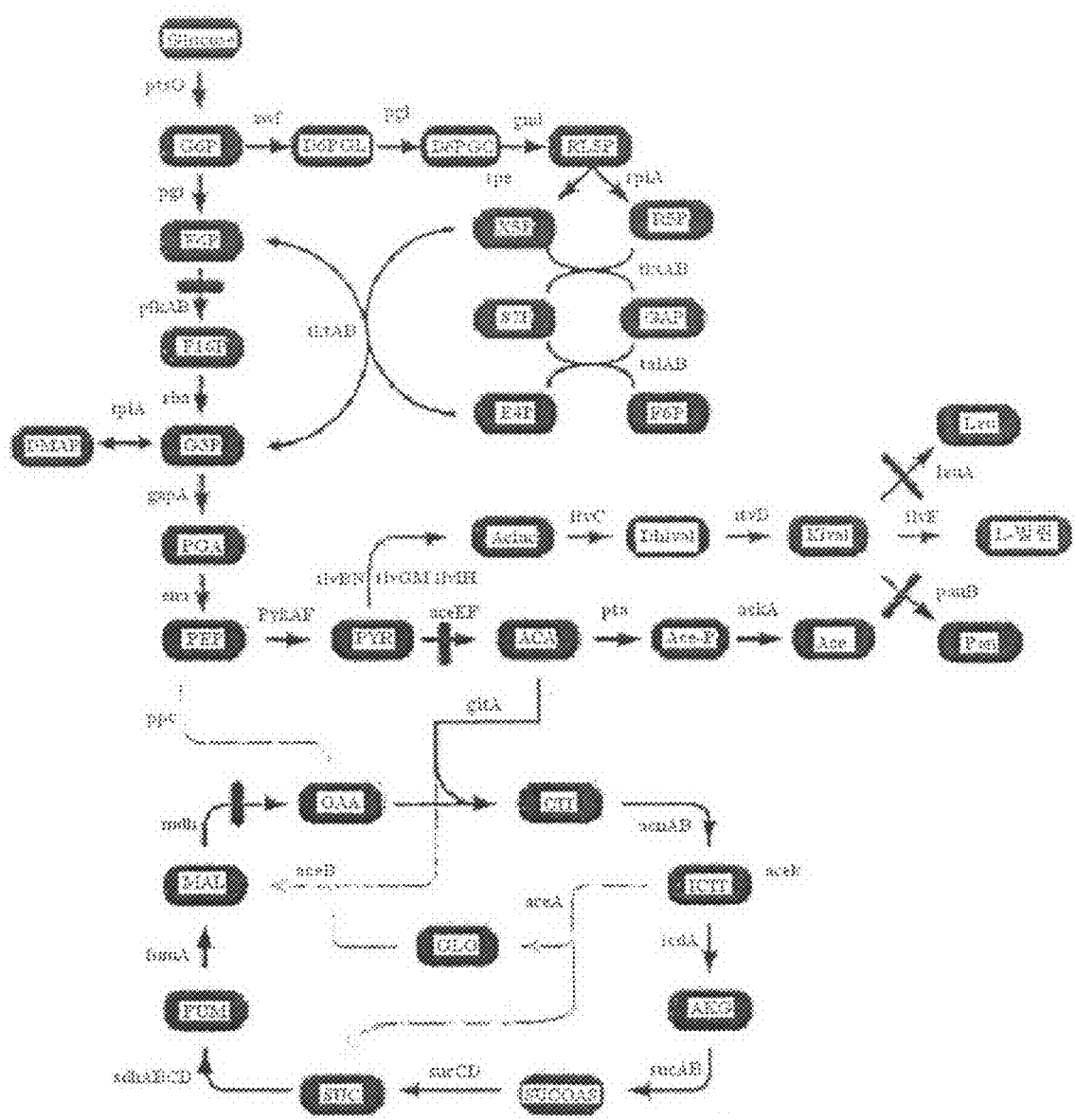
FIG. 2 shows the metabolic pathway of mutant microorganism VAMF obtained by deleting aceF, mdh and pfkA genes from L-valine-producing E. coli microorganisms.

Currently, most amino acid-producing microorganisms are being produced by random mutagenesis or the amplification of the terminal enzymes of biosynthesis pathways. Such methods have the effect of increasing amino acid production efficiency by imparting resistance against the relevant amino acids to the microorganisms and increasing the concentration of biosynthesis enzymes in the microorganisms. However, it is impossible to ensure productivity higher than a given level, because there is a limitation in the availability of a precursor required for amino acid biosynthesis. Therefore, in the present invention, microorganisms having high productivity of L-valine can be produced by controlling intracellular metabolic fluxes in order to facilitate the availability of an L-valine precursor. In order to optimize intracellular metabolic fluxes, the in silico simulation method is used to select a gene (aceF) encoding pyruvate dehydrogenase, a gene (mdh) encoding malate dehydrogenase, and a gene (pfkA) encoding phosphofructokinase, as genes to be deleted. FIG. 2 shows the above-constructed mutant microorganism VAMF with a deletion of aceF, mdh and pfkA genes.

Also, an amino acid exporter is necessary for the production of the relevant amino acid, and particularly, in the case of L-valine, E. coli has a very low charge rate compared to other bacterial strains. For this reason, the amplification of the exporter is required in order to increase the production of L-valine. However, there is a limitation in increasing the efficiency for producing L-valine, because the L-valine exporter is not yet found.

Nicole Kennerknecht et al. reported a protein (BrnFE) serving as an exporter of branched-chain amino acids, including L-valine, in *Corynebacterium glutamicum* (Nicole et al., *J. Bacteriol.*, 184:3947, 2002, U.S. Pat. No. 6,841,360 B2). Also, Ekaterina Alexsandrovna Tabolina et al. reported that said homologous protein also serves as an exporter of L-valine in *E. coli* (US 2005/0239175).

In order to identify the L-valine exporter in the L-valine-producing mutant strain produced in the present invention, the present inventors cloned an ygaZH operon encoding an YgaZH protein. Specifically, the ygaZH operon was amplified by polymerase chain reaction (PCR) using *E. coli* chromosomal DNA as a template with oligonucleotide primers synthesized on the basis of the gene sequence of *E. coli*. The amplified ygaZH gene was digested with NcoI/KpnI and cloned into a pTrc99A expression vector to construct pTrc99AygaZH. The pTrc99AygaZH vector was digested with BspHI/EcoRV, and the resulting gene fragment was inserted into pACYC184 digested with the same enzymes (BspHI/EcoRV), thus constructing expression vector pTrc184ygaZH for overexpressing the ygaZH gene. When the expression vector was introduced into the mutant microorganism (Val+pKBRilvBNCED) having high productivity of L-valine, the L-valine productivity of the mutant microorganism was significantly increased compared to the level suggested by Ekaterina Alexsandrovna Tabolina et al.

Also, based on the fact that global regulator Lrp promotes the expression of an ilvIH operon encoding an acetohydroxy-acid synthase III enzyme which is an important isoenzyme for L-valine biosynthesis (Platko et al., *J. Bacteriol.*, 172:4563-4570, 1990), and inhibits the expression of an livJ gene encoding a transporter involved in the absorption of L-valine (Haney et al., *J. Bacteriol.*, 174:108-115. 1992), the present inventors cloned the lrp gene with the expectation that the amplification of the lrp gene would increase L-valine productivity. Specifically, the lrp gene was amplified by polymerase chain reaction (PCR) using *E. coli* chromosomal DNA as a template with oligonucleotide primer synthesized based on the gene sequence of *E. coli*. The amplified lrp gene was digested with NcoI/KpnI and cloned into a pTrc99A expression vector to construct pTrc99Alrp. The pTrc99Alrp vector was digested with BspHI/EcoRV, and the resulting gene fragment was inserted into pACYC184 digested with the same enzymes (BspHI/EcoRV) to construct expression vector pTrc184lrp for overexpressing the lrp gene, thus confirming that, when the expression vector was introduced into the mutant microorganism (Val+pKBRilvBNCED) having high productivity of L-valine, the L-valine productivity of the microorganism was increased.

EXAMPLES

Hereinafter, the present invention will be described in further detail with reference to examples. However, it will be obvious to those skilled in the art that these examples are illustrative purpose only, and the scope of the present invention is not limited thereto.

Although the following examples describe a method for producing a high concentration of L-valine among branched-chain amino acids by deletion of genes to be deleted in *E. coli* W3110-derived L-valine-producing microorganisms, it will be obvious to those skilled in the art that the genes can also be introduced into other *E. coli* strains and microorganisms, and the strains and the microorganisms can be used to produce not only L-valine, but also L-leucine and L-isoleucine.

Also, although the following examples describe a method of producing a high concentration of L-valine among branched-chain amino acids using ygaZH, isolated and purified from *E. coli* W3110, and a method for producing a vector containing ygaZH, it will be obvious to those skilled in the art that the L-valine exporter can be isolated and purified from other *E. coli* strains and can be used to produce not only L-valine, but also L-leucine and L-isoleucine.

Moreover, although the following examples describe a method of producing transformed microorganisms by introducing a recombinant vector, containing an *E. coli*-derived L-valine exporter gene, into L-valine-producing microorganisms (Val+pKBRilvBNCED) produced based on *E. coli* W3110, and a method for producing L-valine, it will be obvious to those skilled in the art to produce transformed microorganisms by introducing the inventive recombinant vector into host cells having the ability to produce L-valine, selected from the group consisting of bacteria, yeasts and fungi, and produce L-valine from the transformed microorganisms.

In addition, although the following examples illustrate only specific media and culture methods, it will be obvious to those skilled in the art to use glycolytic solution such as whey or CSL (corn steep liquor), and other media, and use various culture methods, such as fed-batch culture or continuous culture, as reported in the literature (Lee et al., *Bioprocess Biosyst. Eng.*, 26:63, 2003; Lee et al., *Appl. Microbiol. Biotechnol.*, 58:663, 2002; Lee et al., *Biotechnol. Lett.*, 25:111, 2003; Lee et al., *Appl. Microbiol. Biotechnol.*, 54:23, 2000; Lee et al., *Biotechnol. Bioeng.*, 72:41, 2001).

Example 1

Construction of Mutant Microorganisms Having High Productivity of L-valine and Measurement of L-valine Productivity 1-1: Construction of Microorganisms Having High Productivity of L-valine
1-1-1: Construction of pSacHR06

Figure 3:
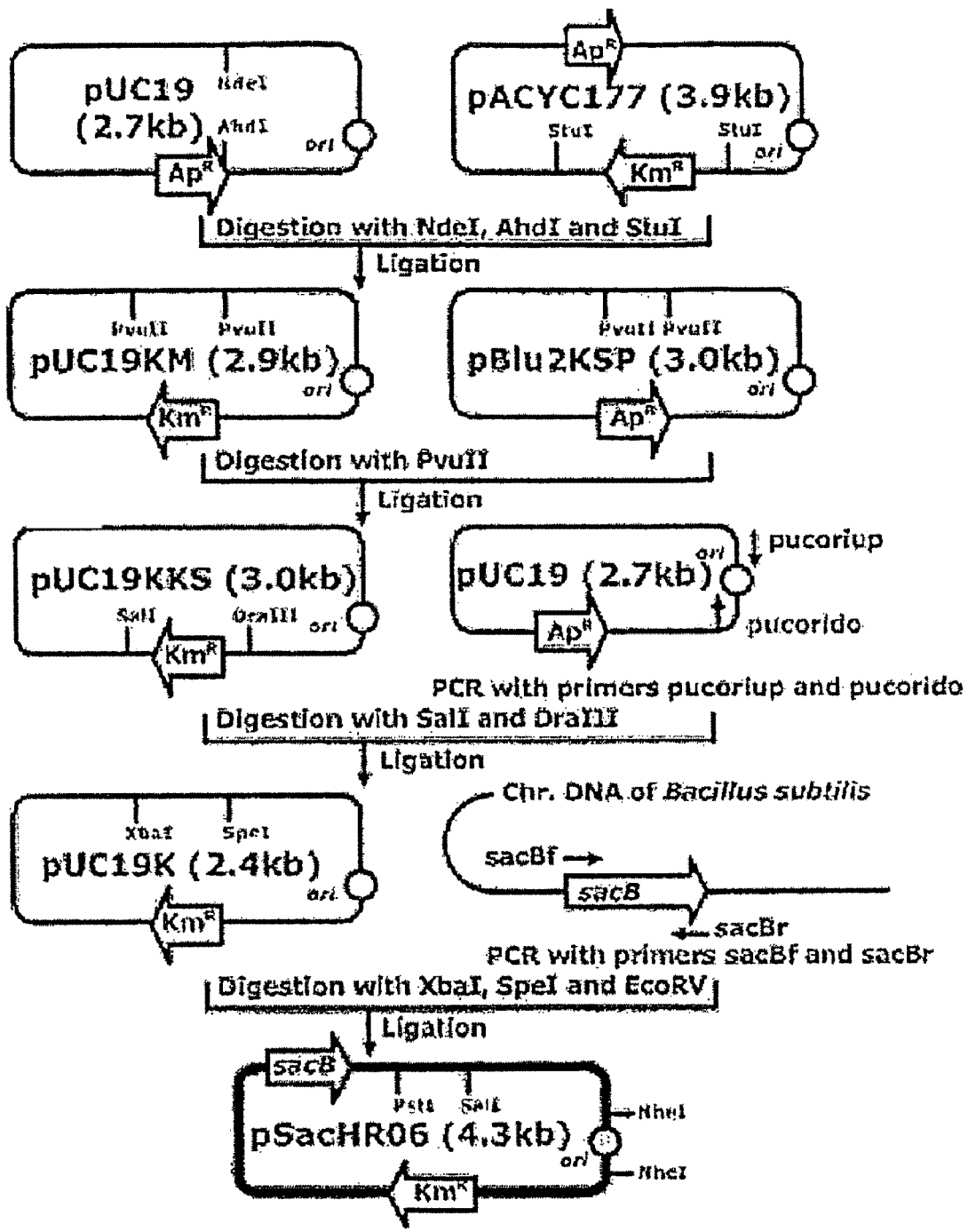
FIG. 3 shows a process for constructing sacB homologous recombination vector pSacHR06 and a genetic map of the vector.

To substitute the specific base or bases of chromosomal DNA, pSacHR06 was constructed for the homologous recombination of *Bacillus subtilis*-derived sacB (Wohlleben et al., *J. Bacteriol.*, 174:5462, 1992) (see FIG. 3). FIG. 3 shows a process of constructing the pSacHR06 vector.

For this purpose, in order to substitute the ampicillin resistance gene of a pUC19 vector (New England Biolab) with kanamycin resistance thereof, a 1.5 kb fragment obtained by digesting the pUC19 vector with NdeI and AhdI was ligated with a 1.3 kb fragment obtained by digesting a pACYC177 vector (New England Biolabs) with StuI, thus obtaining a pUC19KM vector.

Then, a 2.5 kb fragment obtained by digesting the pUC19KM vector with PvuII was ligated with a 400 bp fragment obtained by digesting a pBluescriptIIKS(+) vector with PvuII, thus obtaining a pUC19KKS vector. Then, in order to make it possible to easily remove a DNA replication origin, the pUC19 vector as a template was subjected to PCR using primers of SEQ ID NOs: 1 and 2, thus obtaining a DNA fragment, having a DNA replication origin and the same restriction enzyme recognition sites at both terminal ends thereof, respectively. The fragment was digested with SalI and DraIII and ligated with a 1.5 kb fragment obtained by digesting a pUC19KKS vector with SalI and DraIII, thus obtaining a pUC19K vector. In order to introduce a *Bacillus subtilis* sacB gene into the pUC19K vector, the genomic DNA template of *Bacillus subtilis* was subjected to PCR using primers of SEQ ID NOs: 3 and 4, thus synthesizing a DNA fragment having a sacB gene, and the synthesized DNA fragment and the pUC19K vector were digested with XbaI and SpeI and were ligated with each other, thus constructing a novel vector having a sacB gene. The constructed vector was named "pSacHR06".

The pSacHR06 vector can be used in sacB positive selection, because it has the *Bacillus subtilis*-derived sacB gene, and the removal of the DNA replication origin and the re-ligation of the vector can be easily achieved using restriction enzymes.

SEQ ID NO: 1 (pucoriup)
5'-gccgtcgacgctagcgcatgcacgcgtgtgcacccatgggacgtcct cactgactcgctgcgctc-3'

SEQ ID NO: 2 (pucorido)
5'-ggctcacaacgtggctagcgacgtcgtgcacccatgggttccactga gcgtcagacc-3'

SEQ ID NO: 3 (sacBf):
5'-actctctagacgcgggtttgttactgataa-3'

SEQ ID NO: 4 (sacBr):
5'-gctagatatcaggatatcggcattttcttt-3'

1-1-2: Deletion of lacI Gene

In L-valine-producing microorganism *E. coli* W3110 (ATTC 39936), deletion of lacI gene, which is encoding lac operon repressor and functioning to inhibit the transcription of a lac operon performing lactose degradation, and removal of antibiotic resistance, were performed using primers of SEQ ID NOs: 5 and 6 by a one-step inactivation method (Warner et al., PNAS, 97(12):6640-6645, 2000).

```
SEQ ID NO: 5 (lacI_1stup):
5'-gtgaaaccagtaacgttatacgatgtcgcagagtatgccggtgtctc ttagattgcagcattacacgtcttg-3'

SEQ ID NO: 6 (lacI_1stdo):
5'-tcactgcccgctttccagtcgggaaacctgtcgtgccagctgcatta atgcacttaacggctgacatggg-3'
```

1-1-3: Removal of Feedback Inhibition of ilvH

With reference to U.S. Pat. No. 6,737,255 B2 owned by Ajinomoto Co., Inc., Japan, the $41^{st}$ base (G) and $50^{th}$ base (C) of an ilvH gene encoding acetohydroxy acid synthase isozyme III were substituted with A and T, respectively. Also, the chromosomal DNA of *E. coli* W3110 (ATTC 39936) was isolated and purified according to the known method (Sambrook et al., *Molecular Cloning*, 2nd ed., Cold Spring Harbor Laboratory Press, NY, 1989).

Specifically, PCR was performed using W3110 genomic DNA as a template with primers of SEQ ID NOs: 7 and 8 and primers of SEQ ID NOs: 9 and 10, and the obtained two PCR fragments were mixed with each other at the same concentration. Then, the mixture was subjected to overlapping PCR using primers of SEQ ID NOs: 7 and 10. The obtained 1280-bp PCR fragment was digested with PstI and SalI enzymes and inserted into homologous recombination vector pSacHR06 digested with PstI and SalI enzymes. Then, the PCR fragment was sequenced, and as a result, it was confirmed that the $41^{st}$ base (G) and $50^{th}$ base (C) of ilvH were substituted with A and T, respectively.

The obtained vector was digested with a NheI enzyme to delete replication origin, self-ligated and then electroporated into the electroporation-competent cells of the lacI gene-deleted *E. coli* W3110, constructed in Example 1-1-2. Then, microorganisms, from which feedback inhibition of ilvH has been removed, were collected by sacB positive selection (Wohlleben et al., *J. Bacteriol.*, 174:5462, 1992).

```
SEQ ID NO: 7 (ilvH1):
5'-gactctgcagggtgatcgagactctttggcggttgac-3'

SEQ ID NO: 8 (ilvH2):
5'-ggaaaaaaggccaatcacgcggaataacgcgtctgattcattttcga gtaag-3'

SEQ ID NO: 9 (ilvH3):
5'-cttactcgaaaatgaatcagacgcgttattccgcgtgattggcctt tttcc-3'

SEQ ID NO: 10 (ilvH4):
5'-gctccgtcgaccagtttcacaattgcccctttgcgtaaa-3'
```

1-1-4: Substitution of Attenuators of ilvGMEDA and ilvBN Operons with tac Promoter In order to induce the constitutive expression of acetohydroxy acid synthase isozymes I and II in the *E. coli* W3110, from which the lacI gene and the feedback inhibition of ilvH were removed as described in Example 1-1-3, attenuators involved in the transcription regulatory mechanism of ilvBN and ilvGMEDA operons encoding acetohydroxy acid synthase isozymes I and II, respectively, was substituted with a strong tac promoter.

For the substitution of the ilvGMEDA operon attenuator, PCR was performed using *E. coli* W3110 genomic DNA as a template with a primer pair of SEQ ID NOs: 11 and 12 and a primer pair of SEQ ID NOs: 13 and 14, thus obtaining PCR fragments, ilvGatt1 and ilvGatt2. The obtained two PCR fragments were digested with SaiI/BamHI and EcoRI/PstI enzymes, respectively, and cloned into the corresponding enzyme digestion sites of a pKK223-3 vector (Pharmacia Biotech), and the base sequences of the fragments were analyzed. Then, the sites digested with SalI and PstI enzymes were cloned into the corresponding enzyme digestion sites of the pSacHR06 vectors, and the native promoter containing the attenuator was substituted with a tac promoter in the same manner as in the removal of feedback inhibition.

For the removal of the ilvBN operon attenuator, PCR using a primer pair of SEQ ID NOs: 15 and 16 and a primer pair of SEQ ID NOs: 17 and 18, and cloning, were performed in the same manner as in the removal of the ilvGMEDA attenuator, and then electroporated into the electroporation-competent cells of the *E. coli* W3110, from which the ilvGMEDA attenuator had been removed. As a result, the native promoter containing the ilvBN attenuator could be substituted with a tac promoter.

```
SEQ ID NO: 11 (ilvGatt1f):
5'-gactgtcgacctaacttattggctgtaagctgttctgaggcc-3'

SEQ ID NO: 12 (ilvGatt1r):
5'-gctcggatccgaatgttgttcccttcctcgtagttcatcc-3'

SEQ ID NO: 13 (ilvGatt2f):
5'-gactgaattcatgaatggcgcacagtgggtggtacatgcg-3'

SEQ ID NO: 14 (ilvGatt2r):
5'-gctcctgcagtcaccgctggctaactggatatcttttggg-3'

SEQ ID NO: 15 (ilvBatt1f):
5'-gactcgtcgacagagatggtagggcggataa-3'

SEQ ID NO: 16 (ilvBatt1r):
5'-gctcggatcccacactgtattatgtcaaca-3'

SEQ ID NO: 17 (ilvBatt2f):
5'-gactgaattcatggcaagttcgggcacaac-3'

SEQ ID NO: 18 (ilvBatt2r):
5'-gctcactgcagtgcgtcacgaatgctttctt-3'
```

1-1-5: Deletion of ilvA, panB and leuA Genes

In order to delete ilvA, panB and leuA in the *E. coli* W3110 produced in Example 1-1-4, in which lacI gene and the feedback inhibition of ilvH have been removed and ilvGMEDA and ilvBN operon attenuators have been substituted with tac promoter, primers of SEQ ID NOs: 19 to 24 and the one-step inactivation method (Warner et al., PNAS, 97(12):6640, 2000) mentioned in Example 1-1-2 were used to delete ilvA (gene encoding threonine dehydratase that is the first enzyme in an isoleucine biosynthesis pathway), panB (gene encoding 3-methyl-2-oxobutanoate hydroxymethyltransferase among enzymes required for pantothenate biosynthesis) and leuA (gene encoding 2-isopropylmalate synthase among enzymes required for leucine biosynthesis).

Specifically, the deletion of the three genes was induced in the *E. coli* W3110 electroporation-competent cells constructed in Example 1-1-4, in which the lacI gene and the feedback inhibition of ilvH have been removed and the native promoter containing the ilvGMEDA and ilvBN operon attenuators has been substituted with tac promoter having strong transcription activity.

```
SEQ ID NO: 19 (ilvA1stup):
5'-atggctgactcgcaacccctgtccggtgctccggaaggtgccgaata tttgattgcagcattacacgtcttg-3'

SEQ ID NO: 20 (ilvA1stdo):
5'-ctaacccgccaaaaagaacctgaacgccgggttattggtttcgtcgt ggccacttaacggctgacatggg-3'

SEQ ID NO: 21 (panB1stup):
5'-atgaaaccgaccaccatctccttactgcagaagtacaaacaggaaaa aaagattgcagcattacacgtcttg-3'

SEQ ID NO: 22 (panB1stdo):
5'-ttaatggaaactgtgttcttcgcccggataaacgccggactccactt cagcacttaacggctgacatggg-3'

SEQ ID NO: 23 (leuA1stup):
5'-atgagccagcaagtcattattttcgataccacattgcgcgacggtga acagattgcagcattacacgtcttg-3'

SEQ ID NO: 24 (leuA1stdo):
5'-ttcagaacgtgcaccatggctttggcagatgactcgacaatatcggt agcacttaacggctgacatggg-3'
```

1-1-6: Construction of pKBRilvBNCED Vector

Figure 4:
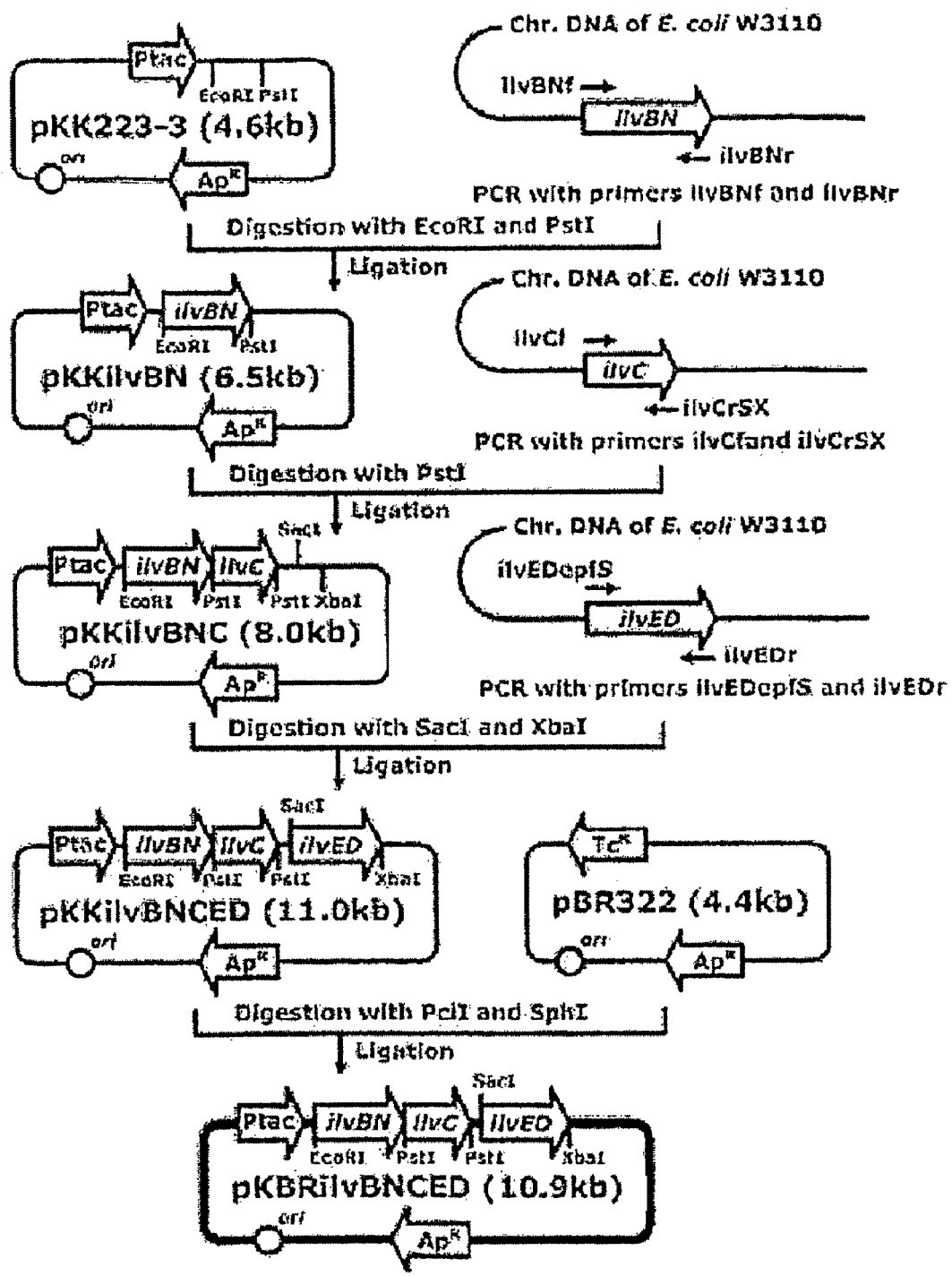
FIG. 4 shows a process for constructing recombinant vector pKBRilvBNCED containing an ilvBNCED gene, and a genetic map of the vector.

Using primers of SEQ ID NOs: 25 to 30, genes essential for the L-valine biosynthesis pathway, that is, ilvB (gene encoding an acetohydroxy acid synthase I large subunit), ilvN (gene encoding an acetohydroxy acid synthase I small subunit), ilvC (gene encoding acetohydroxy acid isomeroreductase), ilvE (gene encoding branched chain amino acid aminotransferase) and ilvD (gene encoding dihydroxy-acid dehydratase) were sequentially cloned into a pKK223-3 expression vector (Pharmacia Biotech) to obtain a pKKilvBNCED vector, and the base sequences of the genes were identified by a sequencing method. The pKKilvBNCED vector was digested with PciI and SphI enzymes to obtain a 9.0 kb fragment, which was then ligated with a 1.9 kb fragment obtained by digesting a pBR322 vector with PciI and SphI enzymes, thus obtaining a pKBRilvBNCED vector (FIG. 4).

```
SEQ ID NO: 25 (ilvBNf):
5'-actcgaattcatggcaagttcgggcacaacat-3'

SEQ ID NO: 26 (ilvBNr):
5'-actcgaattcatggcaagttcgggcacaacat-3'

SEQ ID NO: 27 (ilvCf):
5'-agtgctgcagacgaggaatcaccatggctaac-3'

SEQ ID NO: 28 (ilvCrSX):
5'-gctcctgcagtctagagctagcgagctcttaacccgc-3'

SEQ ID NO: 29 (ilvEDepfs):
5'-actcgagctctttccacgtctgctcaatgaatat-3'

SEQ ID NO: 30 (ilvEDr):
5'-tacgtctagattaaccccccagtttcgatttatc-3'
```

1-1-7: Construction of L-valine-producing Microorganism

An L-valine-producing microorganism (Val+pKBRilvBNCED) was constructed by introducing the pKBRilvBNCED vector, constructed in Example 1-1-6, into the E. coli W3110 strain treated according to the processes of Example 1-1-1 to Example 1-1-5, in which the native promoter containing the ilvGMEDA and ilvBN operon attenuators has been substituted with the tac promoter, the feedback inhibition of ilvh has been removed, and the lacI, ilvA, panB and leuA genes have been deleted.

1-2: Measurement of Ability to Produce L-valine

The L-valine-producing microorganisms (Val+pKBRilvBNCED) were screened in an LB plate medium containing 50 µg/ml of ampicillin and 30 µg/ml of chloramphenicol. Each of the transformed strains was inoculated into 30 ml of an LB medium containing 5 g/l of glucose and was precultured at 31° C. for 24 hours. 1 ml of the precultured broth was seeded into a 250-ml baffle flask containing 30 ml of a medium, containing, per liter of distilled water, 50 g of glucose, 4 g of $KH_2PO_4$, 15 g of $(NH_4)_2SO_4.7H_2O$, 20 mg of $MnSO_4.5H_2O$, 2 g of $MgSO_4.7H_2O$, 30 g of $CaCO_3$, 2 g of yeast extract, 262 mg of L-isoleucine, 262 mg of L-leucine, 425 µg of D-pantothenic acid hemicalcium salt and 5 ml of a trace metal solution (containing, per liter of distilled water, 10 g of $FeSO_4.7H_2O$, 1.35 g of $CaCl_2$, 2.25 g of $ZnSO_4.7H_2O$, 0.5 g of $MnSO_4.4H_2O$, 1 g of $CuSO_4.5H_2O$, 0.106 g of $(NH_4)_6Mo_7O_{24}.4H_2O$, 0.23 g $Na_2B_4O_7.10H_2O$, and 10 ml of 35% HCl) and adjusted to a pH of 8.0 with KOH. Then, the precultured broth was cultured at 31° C. and 250 rpm for 48 hours.

The culture broth was collected and the concentration of L-valine in the collected culture broth was measured by HPLC. As a result, as shown in Table 1, L-valine, which was not produced in the W3110 wild-type strain, was produced in the inventive L-valine-producing microorganisms (Val+pKBRilvBNCED) at a concentration of 3.73 g/l. From such results, it could be seen that the substitution of the attenuator-containing native promoter with the strong tac promoter, and the deletion of competent genes, according to the present invention, played an important role in increasing the L-valine productivity of the microorganisms.

TABLE 1

| Strain | L-valine (g/l) |
| --- | --- |
| W3110 | ND[1] |
| Val + pKBRilvBNCED | 3.73 |

[1]Not detected.

Example 2

Screening of Genes to be Deleted, by In Silico Simulation

In order to further increase the L-valine productivity of the L-valine-producing microorganisms (Val+pKBRilvBNCED) constructed in Example 1-1, genes to be deleted in order to optimize metabolic flux for L-valine production were screened using the in silico simulation method. The in silico stimulation of this Examples was performed with reference to the method described in WO 2006/107127, filed in the name of this applicant. Specifically, simulation on a multi-gene mutant for each gene combination was performed to compare predicted L-valine production rates, thus screening candidate genes showing the highest L-valine production rate.

2-1: Construction of Metabolic Pathways Based on Val Strain

In the present invention, a new metabolic flux analysis system for E. coli mutant microorganisms for producing L-valine was constructed. The system included most of the E. coli metabolic pathways, and medium conditions for the L-valine-producing microorganism (Val+pKBRilvBNCED)

constructed in Example 1 were all reflected in the metabolic pathways. The constructed metabolic pathways were used to make one or more combinations of genes. Such candidate genes in the target strain for producing L-valine were inactivated in simulation using a metabolic flux analysis program, and in this state, the specific growth rate and the useful substance formation rate were predicted. Among these genes, genes showing the highest efficiency were screened.

2-2: Simulation of Multi-gene Mutant Microorganisms

In order to mathematically express the metabolic pathway constructed in Example 2-1, the metabolic flux vector ($v_j$, the flux of the $j^{th}$ reaction) can be calculated using all metabolites, metabolic pathways and the stoichiometric matrix in the pathways ($S_{ij}$, stoichiometric coefficient with time of the $i^{th}$ metabolite in the $j^{th}$ reaction), in which the change in the metabolite concentration X with time can be expressed as the sum of all metabolic fluxes. Also, assuming that the change in X with time is constant, that is, under the assumption of the quasi-steady state, the change in metabolite concentration with time can be defined by the following equation 1:

$$S \cdot v = \frac{dX}{dt} = 0 \quad \text{[Equation 1]}$$

wherein S·v is the change in X with time, X is metabolite concentration, and t is time.

In order to perform simulation on a multi-gene mutant for each gene combination, simulations on various combinations of mutations should be performed. For this purpose, in silico gene knockout simulation was performed to find a group of genes, which showed the highest L-valine production rate when a single gene was deleted (Table 2). The simulation was performed using MetaFluxNet which could be downloaded from the website http://mbel.kaist.ac.kr/ (Lee et al., *Bioinformatics*, 19:2144, 2003).

As a result, as shown in Table 2, it could be seen that, in the case where one or more genes selected from the group consisting of aceE, aceF, lpdA, pfkA, pfkB, tpiA, sdhA, sdhB, sdhC, sdhD, fumA, fumB, fumC, eptB, gpmA, gpmB, ptsG, mdh, ppc, pgi, glgC, sucA, sucB, ribA, folE and ackA were deleted from a microorganism, the L-valine production rate of the microorganism was significantly increased compared to that of the reference strain L-valine-producing microorganism (Val+pKBRilvBNCED) constructed in Example 1, even when a single gene was deleted.

In order to find an optimal combination of the genes that further increases L-valine production rate and production efficiency, the present inventors performed simulation on multi-gene mutant microorganisms using the known sequential multi-gene simulation method (Segre et al., *PNAS*, 99:15112-15117. 2002). Specifically, the L-valine production rates predicted from the deletion of a single gene were compared to screen candidate genes showing the highest L-valine production rate (see Table 2).

Specifically, in a state in which the candidate genes screened in the first simulation were inactivated in simulation, the L-valine production rates predicted according to the deletion of another single gene were compared to screen candidate genes showing the highest L-valine production rate. Then, in a state in which the candidate genes thus determined were inactivated in simulation, the L-valine production rates predicted from the deletion of the next single gene were compared to screen a combination of genes showing the highest L-valine production rate (see Table 2 and FIG. 5).

Figure 5:
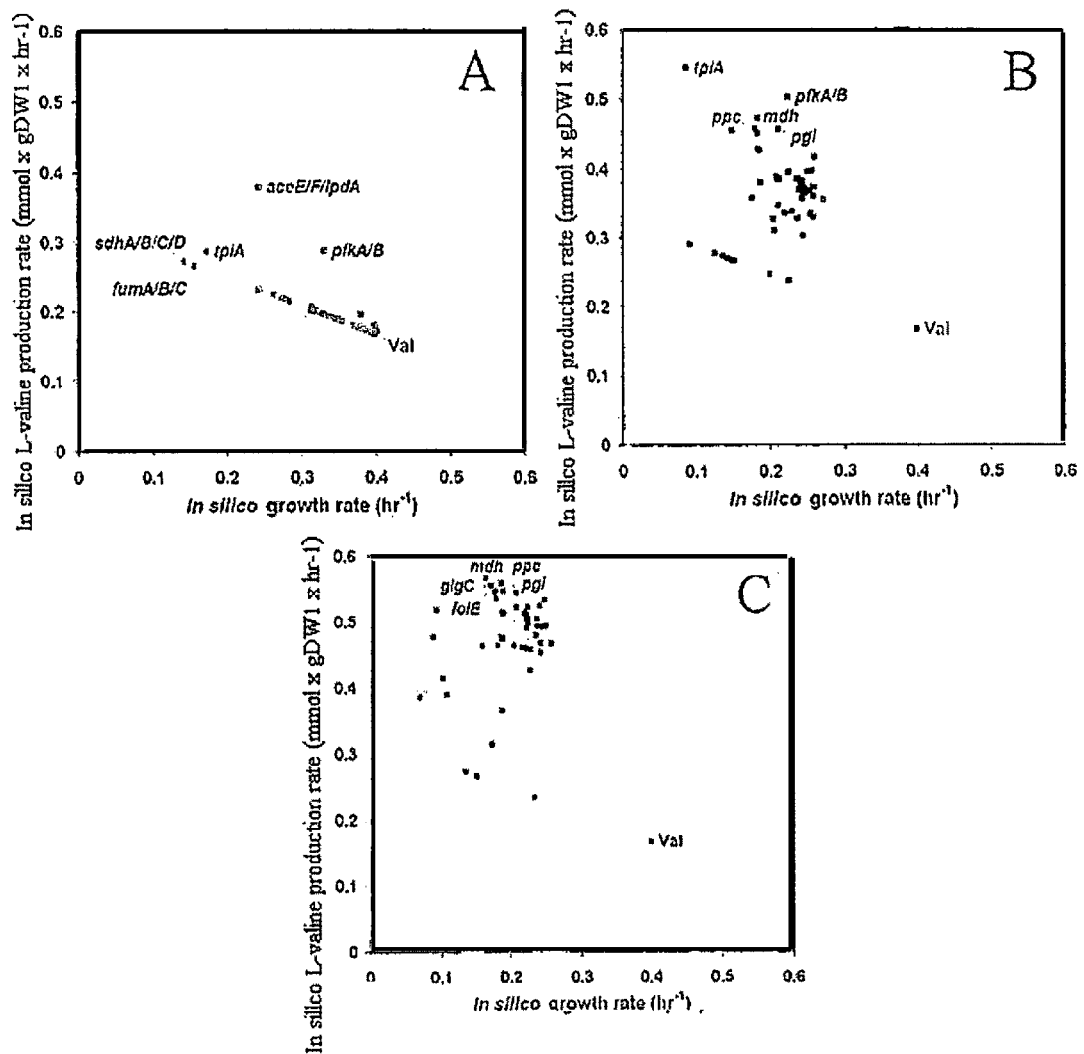
FIG. 5 shows in silico simulation results.

FIG. 5 shows the relationship between L-valine production rate and cell growth rate, caused by the first to third gene deletions performed using the sequential approach method. Specific values for the L-valine production rate and the cell growth rate are shown in Table 2 below.

As can be seen in Table 2, the combination of genes corresponding to the target metabolic pathway showed high production rate compared to the reference strain, even when a single gene was deleted, and the mutant microorganism, from which aceE, aceF and lpdA have been deleted, showed the highest L-valine production rate. Among the aceE, aceF and lpdA genes for sequential simulation, the aceF gene known to have the highest enzymatic activity among genes serving as pyruvate dehydrogenase (Lee et al., *Appl. Microbiol. Biotechnol.*, 65:56-60, 2004) was selected as a first gene to be deleted.

TABLE 2

| Genes to be delated | Predicted growth rate ($hr^{-1}$) | % of control | Predicted L-valine production rate (mmol × $gDW^{-1}$ × $hr^{-1}$) | % of control |
|---|---|---|---|---|
| Control Strain (Val Strain) | 0.4 | 100 | 0.17 | 100 |
| Single knockout | | | | |
| aceE/aceF/lpdA | 0.2432 | 60.81 | 0.3773 | 225.27 |
| pfkA/B | 0.3296 | 82.41 | 0.2867 | 171.19 |
| tpiA | 0.1722 | 43.04 | 0.2866 | 171.08 |
| sdhA/B/C/D | 0.1427 | 35.67 | 0.2712 | 161.94 |
| fumA/B/C | 0.1575 | 39.39 | 0.2653 | 158.38 |
| eptB | 0.2432 | 60.81 | 0.2308 | 137.81 |
| gpmA/B | 0.2629 | 65.72 | 0.2229 | 133.09 |
| ptsG | 0.2731 | 68.28 | 0.2188 | 130.63 |
| Double knockout | | | | |
| aceF, tpiA | 0.0882 | 22.06 | 0.5457 | 325.80 |
| aceF, pfkA/B | 0.2255 | 56.37 | 0.5041 | 300.95 |
| aceF, mdh | 0.1842 | 46.05 | 0.4741 | 283.04 |
| aceF, ppc | 0.1806 | 45.15 | 0.4592 | 274.19 |
| aceF, pgi | 0.2127 | 53.18 | 0.4576 | 273.21 |
| aceF, glgC | 0.1495 | 37.38 | 0.4571 | 272.89 |
| aceF, sucA/B/lpdA | 0.1836 | 45.89 | 0.4520 | 269.88 |
| aceF, ribA | 0.1869 | 46.73 | 0.4278 | 255.41 |
| aceF, folE | 0.1869 | 46.73 | 0.4275 | 255.25 |
| aceF, ackA | 0.2604 | 65.11 | 0.4171 | 249.01 |
| Triple knockout | | | | |
| aceF, pfkA, mdh | 0.1650 | 41.24 | 0.5683 | 339.30 |
| aceF, pfkA, ppc | 0.1883 | 47.08 | 0.5594 | 333.98 |
| aceF, pfkA, glgC | 0.1737 | 43.42 | 0.5554 | 331.58 |
| aceF, pfkA, pgi | 0.1911 | 47.78 | 0.5481 | 327.22 |
| aceF, pfkA, folE | 0.1808 | 45.20 | 0.5479 | 327.12 |

The gene deletion simulations were performed by deleting other candidate genes in addition to aceF. As a result, as shown in Table 2, the deletion of aceF and tpiA resulted in the highest L-valine production rate. However, it was expected that the deletion of the tpiA gene would lead to a great decrease in cell growth rate as shown in Table 2. For this reason, pfkA and pfkB showing the second highest L-valine production rate were determined as candidate genes, and among them, the pfkA gene accounting for 90% of the activity of 6-phosphofructokinase-1 was selected as a second gene to be deleted (Daldal, F., *J. Mol. Biol.*, 168:285-305. 1983).

Simulations on the deletion of three genes including aceF and pfkA were performed and, as a result, the deletion of mdh showed the highest L-valine production rate. Thus, mdh was selected as a third gene to be deleted. Meanwhile, although additional gene deletion simulations would be performed to find candidate groups showing L-valine productivity, additional gene deletion simulations were not performed, because the predicted growth rates in Table 2 were decreased as a result of the deletion of the genes. Accordingly, based on the in silico simulation results, aceF, pfk and mdh were finally selected as genes to be deleted.

Example 3

Additional Deletion of aceF, pfkA and mdh and Measurement of L-valine Productivity 3-1: Additional Deletion of aceF, mdh and pfkA A high-performance, L-valine-producing microorganism (VAMF+pKBRilvBNCED) was constructed by deleting the genes, selected in Example 2, from the L-valine-producing microorganism constructed in Example 1-1-7.

For this purpose, aceF (gene encoding pyruvate dehydrogenase), mdh (gene encoding malate dehydrogenase) and pfkA (gene encoding phosphofructokinase) were deleted using primers of SEQ ID NOs: 31 to 36 according to the one-step inactivation method (Warner et al., *PNAS*, 97(12): 6640, 2000) described in Example 1. Specifically, the high-performance, L-valine-producing microorganism (VAMF+pKBRilvBNCED) was constructed by deleting the three genes from the *E. coli* W3110 mutant microorganism constructed in Example 1-1-5, and then introducing the pKBRilvBNCED vector, constructed in Example 1-1-6, into the microorganism.

```
SEQ ID NO: 31 (aceF1stup):
5'-ttgaagccgaacagtcgctgatcaccgtagaaggcgacaaagcctct
atggattgcagcattacacgtcttg-3'

SEQ ID NO: 32 (aceF1stdo):
5'-aaggagagagaaatcggcagcatcagacgcggcacgaactctttacc
attcacttaacggctgacatggga-3'

SEQ ID NO: 33 (mdh1stup):
5'-atgaaagtcgcagtcctcggcgctgctggcggtattggccaggcgct
tgcgattgcagcattacacgtcttg-3'

SEQ ID NO: 34 (mdh1stdo):
5'-ttacttattaacgaactcttcgcccagggcgatatctttcttcagcg
tatcacttaacggctgacatggga-3'

SEQ ID NO: 35 (pfkA1stup):
5'-atgattaagaaaatcggtgtgttgacaagcggcggtgatgcgccagg
catgattgcagcattacacgtcttg-3'

SEQ ID NO: 36 (pfkA1stdo):
5'-ttaatacagttttttcgcgcagtccagccagtcacctttgaacggac
gctcacttaacggctgacatggga-3'
```

3-2: Measurement of L-valine Productivity

The L-valine-producing microorganism (Val+pKBRilvBNCED) constructed in Example 3-1 was screened in an LB plate medium containing 50 µg/l of ampicillin and 30 µg/ml of chloramphenicol. The transformed strain was inoculated into 30 ml of an LB medium containing 5 g/l of glucose and precultured at 31° C. for 24 hours. Then, 1 ml of the precultured broth was inoculated into a 250-ml baffle flask, containing, per liter of distilled water, 50 g of glucose, 4 g of $KH_2PO_4$, 15 g of $(NH_4)_2SO_4.7H_2O$, 20 mg of $MnSO_4.5H_2O$, 2 g of $MgSO_4.7H_2O$, 30 g of $CaCO_3$, 2 g of yeast extract, 262 mg of L-isoleucine, 262 mg of L-leucine, 425 µg of D-pantothenic acid hemicalcium salt and 5 ml of a trace metal solution (containing, per liter of distilled water, 10 g of $FeSO_4.7H_2O$, 1.35 g of $CaCl_2$, 2.25 g of $ZnSO_4.7H_2O$, 0.5 g of $MnSO_4.4H_2O$, 1 g of $CuSO_4.5H_2O$, 0.106 g of $(NH_4)_6Mo_7O_{24}.4H_2O$, 0.23 g of $Na_2B_4O_7 10H_2O$ and 10 ml of 35% HCl) and adjusted to a pH of 8.0 with KOH, and the inoculated precultured broth was cultured at 31° C. and 250 rpm for 48 hours. To the VAMF strain, 3 g/l of sodium acetate was added.

The culture broth was collected, and the concentration of L-valine in the collected culture broth was measured with an amino acid analyzer (Sykam S433; Sykam GmbH, Eresing, Germany). As a result, as shown in Table 3, the concentration of L-valine in the culture broth of the L-valine-producing microorganisms, from which the genes (aceF, mdh and pfkA) have not been deleted, was 3.73 g/l, and the concentration of L-valine in the culture broth of the L-valine producing microorganisms, from which the genes (aceF, mdh and pfkA) have been deleted, was 4.22 g/e, which corresponded to an increase of about 13.1% compared to the L-valine concentration (3.73 g/l) in the L-valine-producing microorganisms, from which the genes have not been deleted. From such results, it could be seen that metabolic flux control by the introduction of the genes to be deleted played an important role in increasing the L-valine productivity.

TABLE 3

| Strain | L-valine (g/l) |
| --- | --- |
| Val + pKBRilvBNCED | 3.73 |
| VAMF + pKBRilvBNCED | 4.22 |

Example 4

Introduction of Recombinant Vector, Containing *E. coli* ygaZH Operon, into L-valine-producing Microorganisms, and Measurement of L-valine Productivity 4-1: Construction of Recombinant Vector (pTrc184ygaZH) Containing *E. coli* ygaZH Operon The chromosomal DNA of *E. coli* W3110 (ATTC 39936) was isolated and purified according to the known method (Sambrook et al., *Molecular Cloning*, 2nd ed., Cold Spring Harbor Laboratory Press, NY, 1989). PCR was performed using the purified DNA sequence as a template with primers of SEQ ID NOs: 37 and 38, thus obtained a PCR fragment. The PCR reaction was performed under the following conditions: 24 cycles of denaturation at 95° C. for 20 sec, annealing at 55° C. for 30 sec and extension at 72° C. for 80 sec.

```
SEQ ID NO: 37 (ygaZHf):
5'-actaccatggaaagccctactccaca-3'

SEQ ID NO: 38 (ygaZHr):
5'-gctcggtaccttatataatcgccatcactt-3'
```

The amplified PCR fragment (ygaZH gene) was digested with NcoI and KpnI and cloned into a pTrc99A expression vector (Amersham Pharmacia Biotech) to construct pTrc99AygaZH.

Figure 6:
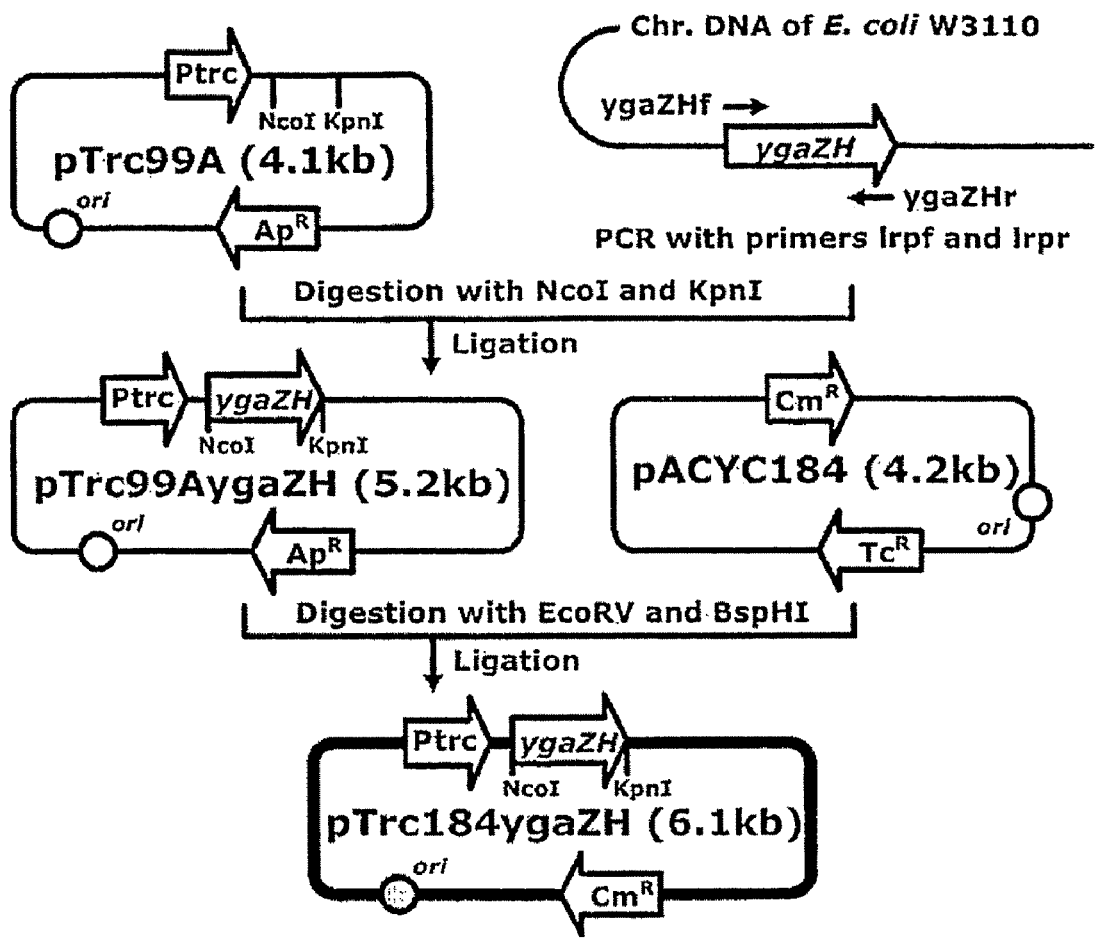
FIG. 6 shows a genetic map of recombinant vector pTrc184ygaZH containing an ygaZH gene.

The pTrc99AygaZH vector was digested with BspHI and EcoRV, and the resulting gene fragment was inserted into pACYC184 (New England Biolabs) digested with the same enzymes, thus constructing expression vector pTrc184ygaZH for expressing the ygaZH gene (FIG. 6).

4-2: Introduction of Recombinant Vector (pTrc184ygaZH) into L-valine-producing Microorganism The vector pTrc184ygaZH constructed in Example 4-1 was introduced into the L-valine-10 producing microorganism Val+pKBRilvBNCED constructed in Example 1, thus constructing recombinant *E. coli* (Val+pKBrilvBNCED+pTrc184ygaZH).

4-3: Measurement of L-valine Productivity

The L-valine-producing *E. coli* bacteria (Val+pKBrilvBNCED+pTrc184ygaZH), constructed in Example 4-2, were screened in an LB plate medium containing 50 μg/ml of ampicillin and 30 μg/ml of chloramphenicol. Each of the transformed strains was inoculated in 30 ml. of an LB medium containing 5 g/l glucose and was precultured at 31° C. for 24 hours. Then, 1 ml of the precultured broth was inoculated into a 250-ml baffle medium, containing, per liter of distilled water, 50 g of glucose, 4 g of $KH_2PO_4$, 15 g of $(NH_4)_2SO_4.7H_2O$, 20 mg of $MnSO_4.5H_2O$, 2 g of $MgSO_4.7H_2O$, 30 g of $CaCO_3$, 2 g of yeast extract, 262 mg of L-isoleucine, 262 mg of L-leucine, 425 μg of D-pantothenic acid hemicalcium salt and 5 ml of a trace metal solution (containing, per liter of distilled water, 10 g of $FeSO_4.7H_2O$, 1.35 g of $CaCl_2$, 2.25 g of $ZnSO_4.7H_2O$, 0.5 g of $MnSO_4.4H_2O$, 1 g of $CuSO_4.5H_2O$, 0.106 g of $(NH_4)_6Mo_7O_{24}.4H_2O$, 0.23 g of $Na_2B_4O_7.10H_2O$, and 10 ml of 35% HCl) and adjusted to a pH of 8.0 with KOH, and the inoculated precultured broth was cultured at 31° C. and 250 rpm for 48 hours.

The medium was collected, and the concentration of L-valine in the medium was measured with an amino acid analyzer. As a result, as can be seen in Table 4, the production of L-valine was increased in the microorganism Val+pKBrilvBNCED+pTrc184ygaZH having the exporter introduced therein, compared to the microorganism Val+pKBrilvBNCED. Such result suggests that the overexpression of the ygaZH gene plays an important role in increasing the production of L-valine.

TABLE 4

| Strain | L-valine (g/l) |
| --- | --- |
| Val + pKBRilvBNCED | 3.73 |
| Val + pKBRilvBNCED + pTrc184ygaZH | 5.25 |

Example 5

Introduction of Recombinant Vector Containing *E. coli* lrp Gene, into L-valine-producing Microorganism, and Measurement of L-valine Productivity 5-1: Construction of Recombinant Vector (pTrc184lrp) Containing *E. coli* lrp Gene The chromosomal DNA of *E. coli* W3110 (ATTC 39936) was isolated and purified according to the known method (Sambrook et al., *Molecular Cloning*, 2nd ed., Cold Spring Harbor Laboratory Press, NY, 1989). PCR was performed using the purified DNA sequence as a template with primers of SEQ ID NOs: 39 and 40, thus obtaining a PCR fragment. The PCR reaction was performed under the following conditions: 24 cycles of denaturation at 95° C. for 20 sec, annealing at 55° C. for 30 sec and extension at 72° C. for 80 sec.

```
SEQ ID NO: 39 (lrpf):
5'-actgccatggtagatagcaagaagcgcc-3'

SEQ ID NO: 40 (lrpr):
5'-gctcggtaccttagcgcgtcttaataacca-3'
```

Figure 7:
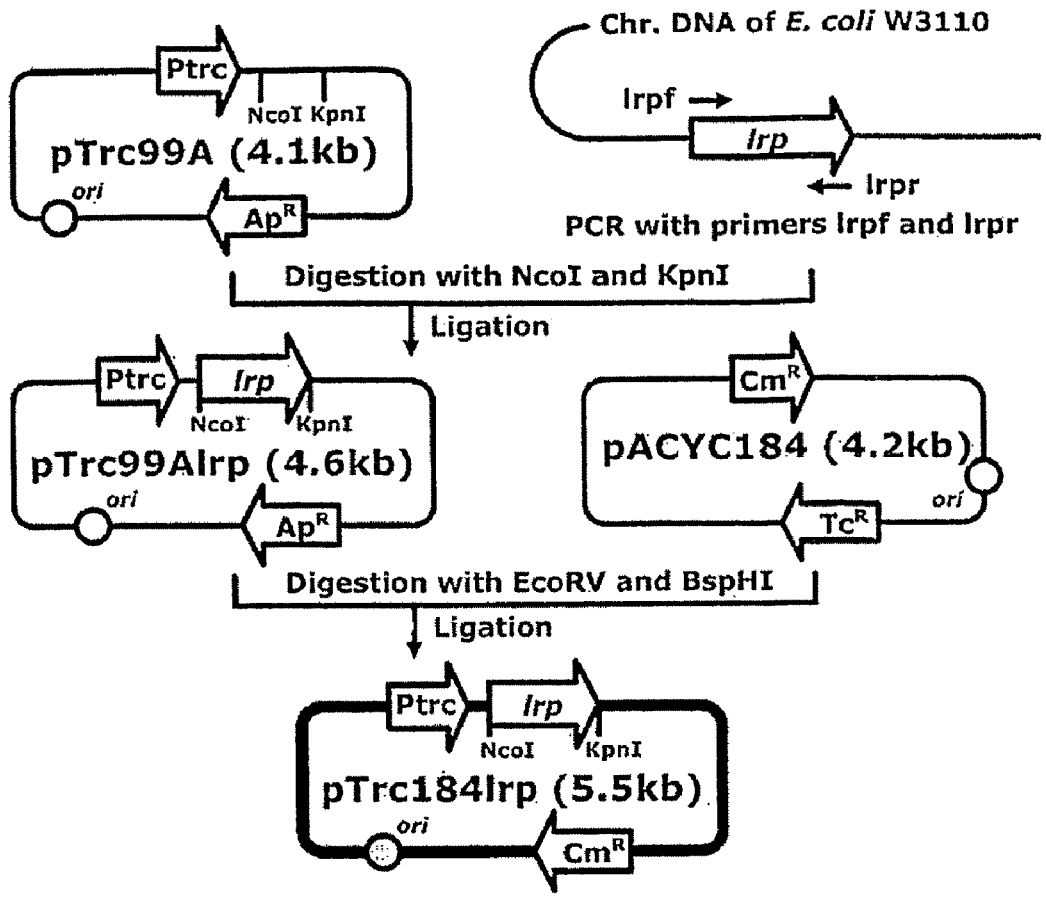
FIG. 7 shows a genetic map of recombinant vector pTrc184lrp containing an lrp gene.

The amplified PCR fragment (lrp gene) was digested with NcoI and KpnI and cloned into a pTrc99A expression vector (Amersham Pharmacia Biotech) to construct pTrc99Alrp. The pTrc99Alrp vector was digested with BspHI and EcoRV, and the resulting gene fragment was inserted into pACYC184 (New England Biolabs) digested with the same enzymes, thus constructing expression vector pTrc184lrp for expressing the lrp (FIG. 7).

5-2: Introduction of Recombinant Vector (pTrc184lrp) into L-valine-producing Microorganism The vector pTrc184lrp constructed in Example 5-1 was introduced into the L-valine-producing microorganism Val+pKBRilvBNCED constructed in Example 1, thus constructing a recombinant *E. coli* strain (Val+pKBrilvBNCED+pTrc184ygaZH).

5-3: Measurement of L-valine Productivity

The L-valine-producing *E. coli* strain (Val+pKBRilvBNCED+pTrc184lrp) constructed in Example 5-1 was screened in an LB medium containing 50 μg/ml of ampicillin and 30 μg/ml of chloramphenicol. Each of the transformed strains was inoculated into 30 ml of an LB medium containing 5 g/l of glucose and was precultured at 31° C. for 24 hours. Then, 1 ml of the precultured broth was inoculated into a 250-ml baffle flask containing 30 ml of a medium, containing, per liter of distilled water, 50 g of glucose, 4 g of $KH_2PO_4$, 15 g $(NH_4)_2SO_4.7H_2O$, 20 mg of $MnSO_4.5H_2O$, 2 g of $MgSO_4.7H_2O$, 30 g of $CaCO_3$, 2 g of yeast extract, 262 mg of L-isoleucine, 262 mg of L-leucine, 425 μg of D-pantothenic acid hemicalcium salt and 5 ml of a trace metal solution (containing, per liter of distilled water, 10 g of $FeSO_4.7H_2O$, 1.35 g $CaCl_2$, 2.25 g of $ZnSO_4.7H_2O$, 0.5 g of $MnSO_4.4H_2O$, 1 g of $CuSO_4.5H_2O$, 0.106 g of $(NH_4)_6Mo_7O_{24}.4H_2O$, 0.23 g of $Na_2B_4O_7.10H_2O$ and 10 ml of 35% HCl) and adjusted to a pH of 8.0 with KOH, and the inoculated precultured broth was cultured at 31° C. and 250 rpm for 48 hours.

The culture broth was collected, and the concentration of L-valine in the collected medium was measured with an amino acid analyzer. As a result, as can be seen in Table 5, the production of L-valine was increased in the microorganism Val+pKBrilvBNCED+pTrc184lrp having the lrp introduced therein, compared to the microorganism Val+pKBRilvBNCED. Such result suggests that the overexpression of the lrp gene plays an important role in increasing the production of L-valine.

TABLE 5

| Strain | L-valine (g/l) |
| --- | --- |
| Val + pKBRilvBNCED | 3.73 |
| Val + pKBRilvBNCED + pTrc184lrp | 4.34 |

Example 6

Introduction of Recombinant Vector Containing Both *E. coli* ygaZH Operon and lrp Gene, into L-valine-producing Microorganism, and Measurement of L-valine Productivity 6-1: Construction of Recombinant Vector (pTrc184ygaZHlrp) Containing Both *E. coli* ygaZH Operon and lrp Gene The chromosomal DNA of *E. coli* W3110 (ATTC 39936) was isolated and purified according to the known method (Sambrook, et al., *Molecular cloning*, 2nd ed, Cold Spring Harbor Laboratory Press, NY, 1989). PCR was performed using the purified DNA sequence as a template with primers of SEQ ID NOs: 41 and 42, thus obtaining a PCR fragment. The PCR reaction was performed under the following conditions: 24 cycles of denaturation at 95° C. for 20 sec, annealing at 55° C. for 30 sec and extension at 72° C. for 80 sec.

SEQ ID NO: 41 (lrpacfb):
5'-atgcggatccgaacagtgatgtttcagggt-3'

SEQ ID NO: 42 (lrpacrp):
5'-atctctgcaggttccgtgttagcgcgtctt-3'

Figure 8:
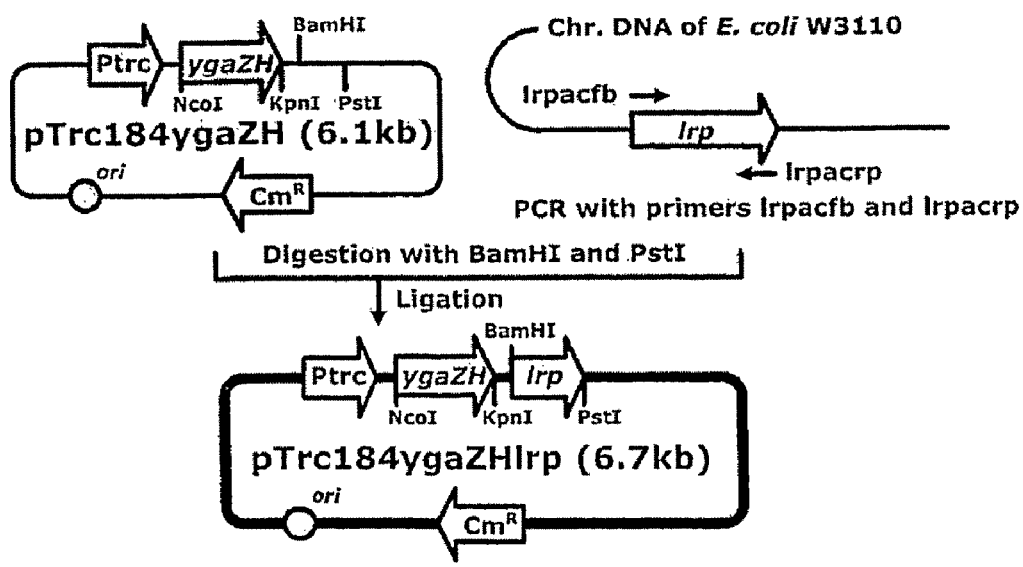
FIG. 8 shows a genetic map of recombinant vector pTrc184ygaZHlrp containing both an ygaZH gene and an lrp gene.

The amplified PCR fragment (lrp gene) was digested with BamHI and PstI and inserted into the gene fragment obtained by digesting the vector pTrc184ygaZH, constructed in Example 4-1, with the same enzymes, thus constructing recombinant vector pTrc184ygaZHlrp containing both the ygaZH operon and the lrp gene (FIG. 8).

6-2: Introduction of Recombinant Vector (pTrc184ygaZHlrp) into L-valine-producing Microorganisms The vector pTrc184ygaZHlrp constructed in Example 6-1 was introduced in the L-valine-producing microorganism Val+pKBRilvBNCED constructed in Example 1, thus constructing recombinant E. coli (Val+pKBRilvBNCED+pTrc184ygaZHlrp).

6-3: Measurement of L-valine Productivity

The L-valine-producing E. coli (Val+pKBRilvBNCED+pTrc184ygaZHlrp) constructed in Example 6-2 was screened in an LB plate medium containing 50 μg/ml of ampicillin and 30 μg/ml of chloramphenicol. The transformed strain was inoculated into 30 ml of an LB medium containing 5 g/l of glucose and was precultured at 31° C. for 24 hours. Then, 1 ml of the precultured broth was inoculated into a 250-ml baffle flask containing 30 ml of a medium, containing, per liter of distilled water, 50 g of glucose, 4 g of $KH_2PO_4$, 15 g of $(NH_4)_2SO_4.7H_2O$, 20 mg of $MnSO_4.5H_2O$, 2 g of $MgSO_4.7H_2O$, 30 g of $CaCO_3$, 2 g of yeast extract, 262 mg of L-isoleucine, 262 mg of L-leucine, 425 μg of D-pantothenic acid hemicalcium salt and 5 ml of a trace metal solution (containing, per liter of distilled water, 10 g of $FeSO_4.7H_2O$, 1.35 g of $CaCl_2$, 2.25 g of $ZnSO_4.7H_2O$, 0.5 g of $MnSO_4.4H_2O$, 1 g of $CuSO_4$ $5H_2O$, 0.106 g of $(NH_4)_6Mo_7O_{24}.4H_2O$, 0.23 g of $Na_2B_4O_7.10H_2O$ and 10 ml of 35% HCl) and adjusted to a pH of 8.0 with KCl, and the inoculated precultured broth was cultured at 31° C. and 250 rpm for 48 hours.

The medium was collected, and the concentration of L-valine in the collected medium was measured with an amino acid analyzer. As a result, as can be seen in Table 6, the production of L-valine was increased in the microorganism Val+pKBRilvBNCED+pTrc184ygaZHlrp containing both the ygaZH operon and the lrp gene, compared to the microorganisms Val+pKBRilvBNCED, Val+pKBRilvBNCED+pTrc184ygaZH, and Val+pKBRilvBNCED+pTrc184lrp. Such result suggests that the simultaneous overexpression of the ygaZH operon and the lrp gene plays an important role in increasing the production of L-valine.

TABLE 6

| Strain | L-valine (g/l) |
| --- | --- |
| Val + pKBRilvBNCED | 3.73 |
| Val + pKBRilvBNCED + pTrc184ygaZH | 5.25 |
| Val + pKBRilvBNCED + pTrc184lrp | 4.34 |
| Val + pKBRilvBNCED + pTrc184ygaZHlrp | 7.61 |

Example 7

Introduction of Recombinant Vector, Containing Both E. coli ygaZH Operon and lrp Gene, into High-Performance, L-valine-producing Microorganism having Deletion of aceF, pfkA and mdh Genes and Measurement of L-valine Productivity 7-1: Introduction of Recombinant Vector (pTrc184ygaZHlrp) into High-performance, L-valine-producing Microorganism The vector pTrc184ygaZHlrp constructed in Example 6-1 was introduced into the high-performance, L-valine-producing microorganism VAMF+pKBRilvBNCED constructed in Example 2, thus constructing recombinant E. coli (VAMF+pKBrilvBNCED+pTrc184ygaZHlrp).

7-2: Measurement of L-valine Productivity

The L-valine-producing E. coli (VAMF+pKBRilvBNCED+pTrc184ygaZHlrp) constructed in Example 7-1 was screened in an LB plate medium, containing ampicillin, chloramphenicol and kanamycin in concentrations of 50 μg/ml, 30 μg/ml and 40 μg/ml, respectively. Each of the transformed strain and the strains Val+pKBRilvBNCED, VAMF+pKBRilvBNCED and Val+pKBRilvBNCED+pTrc184ygaZHlrp was inoculated into 200 ml of an LB medium containing 5 g/l of glucose and was precultured at 31° C. for 24 hours. Then, each of the precultured broth was inoculated into a 6.6-liter fermenter (Bioflo 3000, New Brunswick Scientific Co., Edison, N.J., USA) containing 1.8 liters of medium, containing, per liter of distilled water, 20 g of glucose, 2 g of $KH_2PO_4$, 20 g of $(NH_4)_2SO_4.7H_2O$, 0.4 g $MgSO_4.7H_2O$, 1.6 g of NaCl, 2 g of yeast extract, 262 mg of L-isoleucine, 262 mg of L-leucine, 425 μg of D-pantothenic acid hemicalcium salt and 5 ml of a trace metal solution (containing, per liter of distilled water, 10 g of $FeSO_4.7H_2O$, 1.35 g of $CaCl_2$, 2.25 g of $ZnSO_4.7H_2O$, 0.5 g $MnSO_4.4H_2O$, 1 g of $CuSO_4.5H_2O$, 0.106 g of $(NH_4)_6Mo_7O_{24}.4H_2O$, 0.23 g of $Na_2B_4O_7.10H_2O$ and 10 ml of 35% HCl, and each inoculated precultured broth was cultured at 31° C. The pH of each culture broth was maintained at 6.0 by automatic feeding of 25% (v/v) $NH_4OH$, and the dissolved oxygen concentration was maintained at more than 40% of air saturation by automatically controlling the agitation speed to 1000 rpm while supplying air at 1 vvm (air volume/working volume/minute). To the VAMF strain, 3 g/l of sodium acetate was added.

When glucose in each of the medium was completely consumed, as measured with a glucose analyzer (model2700 STAT, Yellow Springs Instrument, Yellow Springs, Ohio, USA), the media were collected, and the concentration of L-valine in the collected media were collected, and the concentrations of L-valine in the collected media were measured with an amino acid analyzer. As a result, as can be seen in Table 7 below, the Val+pKBRilvBNCED+pTrc184ygaZHlrp strain, into which an additional deletion of aceF, pfkA and mdh has been introduced, showed an increase in L-valine production of 126.7%, which was significantly higher than 45.5% for the Val+pKBRilvBNCED strain, into which an additional deletion of aceF, pfkA and mdh has been introduced.

From the above result, it could be seen that the effect of metabolic flux control caused by the additional deletion of aceF, pfkA and mdh was further increased, when the exporter (ygaZH operon) and the global regulator (lrp gene) were simultaneously overexpressed. Also, it could be seen that the metabolic flux control caused by the additional deletion of aceF, pfkA and mdh showed a synergistic effect on the simultaneous overexpression of the exporter (ygaZH operon) and the global regulator (lrp gene), thus further increasing the production of L-valine.

TABLE 7

| Strain | L-valine (g/l) |
| --- | --- |
| Val + pKBRilvBNCED | 2.75 |
| VAMF + pKBRilvBNCED | 4.00 |
| Val + pKBRilvBNCED + pTrc184ygaZHlrp | 3.33 |
| VAMF + pKBRilvBNCED + pTrc184ygaZHlrp | 7.55 |

INDUSTRIAL APPLICABILITY

As described and proved above in detail, the inventive method for producing mutant microorganisms having high productivity of L-valine can effectively provide microorganisms having high productivity of branched-chain amino acids, using the rational design method, which comprises deleting specific genes to reconstruct metabolic pathways and amplifying necessary genes, unlike the prior random mutagenesis methods. Also, the mutant microorganisms according to the present invention can produce branched-chain amino acids with high efficiency by site-specific mutagenesis and metabolic flux control, and particularly can produce L-valine among the branched-chain amino acids, with high efficiency. Accordingly, the mutant microorganisms of the present invention will be useful as industrial microorganisms for producing L-valine.

While the present invention has been described in detail with reference to specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A mutant *Escherichia coli* (*E. coli*) strain for increasing production of L-valine, in which:
   (a) ilvA, leuA and panB are attenuated or deleted;
   (b) lacI gene is deleted;
   (c) feedback inhibition of ilvH gene is removed, wherein the removal of feedback inhibition of ilvH is induced by substitution of residues encoding glycine 14 and serine 17 to encode a small subunit of acetolactate synthase;
   (d) attenuators of ilvGMEDA and ilvBN operons are substituted with tac promoter;
   (e) aceF and pfkA genes are attenuated or deleted;
   (f) the mutant strain comprises an expression vector containing ilvB, ilvN, ilvC, ilvE and ilvD genes from *E. coli*;
   (g) the mutant strain overexpresses lrp gene of SEQ ID NO: 46; and
   (h) the mutant strain overexpresses a branched-chain amino acid exporter gene of SEQ ID NO:45.

2. A mutant *Escherichia coli* (*E. coli*) strain for increasing production of L-valine, in which:
   (a) ilvA, leuA and panB are attenuated or deleted;
   (b) lacI gene is deleted;
   (c) feedback inhibition of ilvH gene is removed, wherein the removal of feedback inhibition of ilvH is induced by substitution of residues encoding glycine 14 and serine 17 to encode a small subunit of acetolactate synthase;
   (d) attenuators of ilvGMEDA and ilvBN operons are substituted with tac promoter;
   (e) aceF, pfkA and mdh genes are attenuated or deleted;
   (f) the mutant strain comprises an expression vector containing ilvB, ilvN, ilvC, ilvE and ilvD genes from *E. coli*;
   (g) the mutant strain overexpresses lrp gene of SEQ ID NO: 46; and
   (h) the mutant strain overexpresses a branched-chain amino acid exporter gene of SEQ ID NO:45.

* * * * *

SEQUENCE LISTING

```
<160> NUMBER OF SEQ ID NOS: 46

<210> SEQ ID NO 1
<211> LENGTH: 66
<212> TYPE: DNA
<213> ORGANISM: Artificial Sequence
<220> FEATURE:
<223> OTHER INFORMATION: primer

<400> SEQUENCE: 1
agccgtcgac gctagcgcat gcacgcgtgt gcacccatgg gacgtcctca ctgactcgct    60
gcgctc                                                               66

<210> SEQ ID NO 2
<211> LENGTH: 57
<212> TYPE: DNA
<213> ORGANISM: Artificial Sequence
<220> FEATURE:
<223> OTHER INFORMATION: primer

<400> SEQUENCE: 2
ggctcacaac gtggctagcg acgtcgtgca cccatgggtt ccactgagcg tcagacc       57

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
actctctaga cgcgggtttg ttactgataa                                     30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gctagatatc aggatatcgg cattttcttt                                     30

<210> SEQ ID NO 5
<211> LENGTH: 72
```

<212> TYPE: DNA
<213> ORGANISM: Artificial Sequence
<220> FEATURE:
<223> OTHER INFORMATION: primer

<400> SEQUENCE: 5
gtgaaaccag taacgttata cgatgtcgca gagtatgccg gtgtctctta gattgcagca    60
ttacacgtct tg                                                        72

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
tcactgcccg ctttccagtc gggaaacctg tcgtgccagc tgcattaatg cacttaacgg    60
ctgacatggg                                                           70

<210> SEQ ID NO 7
<211> LENGTH: 37
<212> TYPE: DNA
<213> ORGANISM: Artificial Sequence
<220> FEATURE:
<223> OTHER INFORMATION: primer

<400> SEQUENCE: 7
gactctgcag ggtgatcgag actctttggc ggttgac                             37

<210> SEQ ID NO 8
<211> LENGTH: 52
<212> TYPE: DNA
<213> ORGANISM: Artificial Sequence
<220> FEATURE:
<223> OTHER INFORMATION: primer

<400> SEQUENCE: 8
ggaaaaaagg ccaatcacgc ggataacgc gtctgattca ttttcgagta ag             52

<210> SEQ ID NO 9
<211> LENGTH: 52
<212> TYPE: DNA
<213> ORGANISM: Artificial Sequence
<220> FEATURE:
<223> OTHER INFORMATION: primer

<400> SEQUENCE: 9
cttactcgaa aatgaatcag acgcgttatt ccgcgtgatt ggcctttttt cc            52

<210> SEQ ID NO 10
<211> LENGTH: 38
<212> TYPE: DNA
<213> ORGANISM: Artificial Sequence
<220> FEATURE:
<223> OTHER INFORMATION: primer

<400> SEQUENCE: 10
gctccgtcga ccagtttcac aattgcccct tgcgtaaa                            38

<210> SEQ ID NO 11
<211> LENGTH: 42
<212> TYPE: DNA
<213> ORGANISM: Artificial Sequence
<220> FEATURE:
<223> OTHER INFORMATION: primer

```
<400> SEQUENCE: 11
gactgtcgac ctaacttatt ggctgtaagc tgttctgagg cc                    42

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
gctcggatcc gaatgttgtt cccttcctcg tagttcatcc                       40

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
gactgaattc atgaatggcg cacagtgggt ggtacatgcg                       40

<210> SEQ ID NO 14
<211> LENGTH: 40
<212> TYPE: DNA
<213> ORGANISM: Artificial Sequence
<220> FEATURE:
<223> OTHER INFORMATION: primer

<400> SEQUENCE: 14
gctcctgcag tcaccgctgg ctaactggat atcttttggg                       40

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
gactcgtcga cagagatggt agggcggata a                                31

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
gctcggatcc cacactgtat tatgtcaaca                                  30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
gactgaattc atggcaagtt cgggcacaac                                  30

<210> SEQ ID NO 18
<211> LENGTH: 31
```

```
<212> TYPE: DNA
<213> ORGANISM: Artificial Sequence
<220> FEATURE:
<223> OTHER INFORMATION: primer

<400> SEQUENCE: 18
gctcactgca gtgcgtcacg aatgctttct t                                    31

<210> SEQ ID NO 19
<211> LENGTH: 72
<212> TYPE: DNA
<213> ORGANISM: Artificial Sequence
<220> FEATURE:
<223> OTHER INFORMATION: primer

<400> SEQUENCE: 19
atggctgact cgcaaccect gtccggtgct ccggaaggtg ccgaatattt gattgcagca    60
ttacacgtct tg                                                         72

<210> SEQ ID NO 20
<211> LENGTH: 70
<212> TYPE: DNA
<213> ORGANISM: Artificial Sequence
<220> FEATURE:
<223> OTHER INFORMATION: primer

<400> SEQUENCE: 20
ctaacccgcc aaaaagaacc tgaacgccgg gttattggtt tcgtcgtggc cacttaacgg    60
ctgacatggg                                                            70

<210> SEQ ID NO 21
<211> LENGTH: 72
<212> TYPE: DNA
<213> ORGANISM: Artificial Sequence
<220> FEATURE:
<223> OTHER INFORMATION: primer

<400> SEQUENCE: 21
atgaaaccga ccaccatctc cttactgcag aagtacaaac aggaaaaaaa gattgcagca    60
ttacacgtct tg                                                         72

<210> SEQ ID NO 22
<211> LENGTH: 70
<212> TYPE: DNA
<213> ORGANISM: Artificial Sequence
<220> FEATURE:
<223> OTHER INFORMATION: primer

<400> SEQUENCE: 22
ttaatggaaa ctgtgttctt cgcccggata aacgccggac tccacttcag cacttaacgg    60
ctgacatggg                                                            70

<210> SEQ ID NO 23
<211> LENGTH: 72
<212> TYPE: DNA
<213> ORGANISM: Artificial Sequence
<220> FEATURE:
<223> OTHER INFORMATION: primer

<400> SEQUENCE: 23
atgagccagc aagtcattat tttcgatacc acattgcgcg acggtgaaca gattgcagca    60
ttacacgtct tg                                                         72
```

<210> SEQ ID NO 24
<211> LENGTH: 69
<212> TYPE: DNA
<213> ORGANISM: Artificial Sequence
<220> FEATURE:
<223> OTHER INFORMATION: primer

<400> SEQUENCE: 24
ttcagaacgt gcaccatggc tttggcagat gactcgacaa tatcggtagc acttaacggc    60
tgacatggg                                                            69

<210> SEQ ID NO 25
<211> LENGTH: 32
<212> TYPE: DNA
<213> ORGANISM: Artificial Sequence
<220> FEATURE:
<223> OTHER INFORMATION: primer

<400> SEQUENCE: 25
actcgaattc atggcaagtt cgggcacaac at                                  32

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
actcgaattc atggcaagtt cgggcacaac at                                  32

<210> SEQ ID NO 27
<211> LENGTH: 32
<212> TYPE: DNA
<213> ORGANISM: Artificial Sequence
<220> FEATURE:
<223> OTHER INFORMATION: primer

<400> SEQUENCE: 27
agtgctgcag acgaggaatc accatggcta ac                                  32

<210> SEQ ID NO 28
<211> LENGTH: 37
<212> TYPE: DNA
<213> ORGANISM: Artificial Sequence
<220> FEATURE:
<223> OTHER INFORMATION: primer

<400> SEQUENCE: 28
gctcctgcag tctagagcta gcgagctctt aacccgc                             37

<210> SEQ ID NO 29
<211> LENGTH: 34
<212> TYPE: DNA
<213> ORGANISM: Artificial Sequence
<220> FEATURE:
<223> OTHER INFORMATION: primer

<400> SEQUENCE: 29
actcgagctc tttccacgtc tgctcaatga atat                                34

<210> SEQ ID NO 30
<211> LENGTH: 34
<212> TYPE: DNA
<213> ORGANISM: Artificial Sequence
<220> FEATURE:
<223> OTHER INFORMATION: primer

```
<400> SEQUENCE: 30
tacgtctaga ttaaccccccc agtttcgatt tatc                                34

<210> SEQ ID NO 31
<211> LENGTH: 72
<212> TYPE: DNA
<213> ORGANISM: Artificial Sequence
<220> FEATURE:
<223> OTHER INFORMATION: primer

<400> SEQUENCE: 31
ttgaagccga acagtcgctg atcaccgtag aaggcgacaa agcctctatg gattgcagca     60
ttacacgtct tg                                                        72

<210> SEQ ID NO 32
<211> LENGTH: 71
<212> TYPE: DNA
<213> ORGANISM: Artificial Sequence
<220> FEATURE:
<223> OTHER INFORMATION: primer

<400> SEQUENCE: 32
aaggagagag aaatcggcag catcagacgc ggcacgaact ctttaccatt cacttaacgg     60
ctgacatggg a                                                         71

<210> SEQ ID NO 33
<211> LENGTH: 72
<212> TYPE: DNA
<213> ORGANISM: Artificial Sequence
<220> FEATURE:
<223> OTHER INFORMATION: primer

<400> SEQUENCE: 33
atgaaagtcg cagtcctcgg cgctgctggc ggtattggcc aggcgcttgc gattgcagca     60
ttacacgtct tg                                                        72

<210> SEQ ID NO 34
<211> LENGTH: 71
<212> TYPE: DNA
<213> ORGANISM: Artificial Sequence
<220> FEATURE:
<223> OTHER INFORMATION: primer

<400> SEQUENCE: 34
ttacttatta acgaactctt cgcccagggc gatatctttc ttcagcgtat cacttaacgg     60
ctgacatggg a                                                         71

<210> SEQ ID NO 35
<211> LENGTH: 72
<212> TYPE: DNA
<213> ORGANISM: Artificial Sequence
<220> FEATURE:
<223> OTHER INFORMATION: primer

<400> SEQUENCE: 35
atgattaaga aaatcggtgt gttgacaagc ggcggtgatg cgccaggcat gattgcagca     60
ttacacgtct tg                                                        72

<210> SEQ ID NO 36
<211> LENGTH: 71
<212> TYPE: DNA
<213> ORGANISM: Artificial Sequence
```

```
<220> FEATURE:
<223> OTHER INFORMATION: primer

<400> SEQUENCE: 36
ttaatacagt tttttcgcgc agtccagcca gtcacctttg aacggacgct cacttaacgg    60
ctgacatggg a                                                        71

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
actaccatgg aaagccctac tccaca                                        26

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
gctcggtacc ttatataatc gccatcactt                                    30

<210> SEQ ID NO 39
<211> LENGTH: 28
<212> TYPE: DNA
<213> ORGANISM: Artificial Sequence
<220> FEATURE:
<223> OTHER INFORMATION: primer

<400> SEQUENCE: 39
actgccatgg tagatagcaa gaagcgcc                                      28

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
gctcggtacc ttagcgcgtc ttaataacca                                    30

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
atgcggatcc gaacagtgat gtttcagggt                                    30

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
atctctgcag gttccgtgtt agcgcgtctt                                    30
```

<210> SEQ ID NO 43
<211> LENGTH: 245
<212> TYPE: PRT
<213> ORGANISM: Escherichia coli

<400> SEQUENCE: 43

Met Glu Ser Pro Thr Pro Gln Pro Ala Pro Gly Ser Ala Thr Phe Met
1               5                   10                  15

Glu Gly Cys Lys Asp Ser Leu Pro Ile Val Ile Ser Tyr Ile Pro Val
                20                  25                  30

Ala Phe Ala Phe Gly Leu Asn Ala Thr Arg Leu Gly Phe Ser Pro Leu
            35                  40                  45

Glu Ser Val Phe Phe Ser Cys Ile Ile Tyr Ala Gly Ala Ser Gln Phe
        50                  55                  60

Val Ile Thr Ala Met Leu Ala Ala Gly Ser Ser Leu Trp Ile Ala Ala
65                  70                  75                  80

Leu Thr Val Met Ala Met Asp Val Arg His Val Leu Tyr Gly Pro Ser
                85                  90                  95

Leu Arg Ser Arg Ile Ile Gln Arg Leu Gln Lys Ser Lys Thr Ala Leu
            100                 105                 110

Trp Ala Phe Gly Leu Thr Asp Glu Val Phe Ala Ala Thr Ala Lys
        115                 120                 125

Leu Val Arg Asn Asn Arg Arg Trp Ser Glu Asn Trp Met Ile Gly Ile
    130                 135                 140

Ala Phe Ser Ser Trp Ser Ser Trp Val Phe Gly Thr Val Ile Gly Ala
145                 150                 155                 160

Phe Ser Gly Ser Gly Leu Leu Gln Gly Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ser Leu Cys Val Thr Ala Ala Leu Val Gly Ala
        195                 200                 205

Leu Ala Gly Val Thr Leu Phe Ser Ile Pro Val Ala Ile Leu Ala Gly
    210                 215                 220

Ile Val Cys Gly Cys Leu Thr Ala Leu Ile Gln Ala Phe Trp Gln Gly
225                 230                 235                 240

Ala Pro Asp Glu Leu
                245

<210> SEQ ID NO 44
<211> LENGTH: 111
<212> TYPE: PRT
<213> ORGANISM: Escherichia coli

<400> SEQUENCE: 44

Met Ser Tyr Glu Val Leu Leu Leu Gly Leu Leu Val Gly Val Ala Asn
1               5                   10                  15

Tyr Cys Phe Arg Tyr Leu Pro Leu Arg Leu Arg Val Gly Asn Ala Arg
                20                  25                  30

Pro Thr Lys Arg Gly Ala Val Gly Ile Leu Leu Asp Thr Ile Gly Ile
            35                  40                  45

Ala Ser Ile Cys Ala Leu Leu Val Ser Thr Ala Pro Glu Val Met
        50                  55                  60

His Asp Thr Arg Arg Phe Val Pro Thr Leu Val Gly Phe Ala Val Leu
65                  70                  75                  80

Gly Ala Ser Phe Tyr Lys Thr Arg Ser Ile Ile Pro Thr Leu Leu
            85                  90                  95

Ser Ala Leu Ala Tyr Gly Leu Ala Trp Lys Val Met Ala Ile Ile
        100                 105                 110

<210> SEQ ID NO 45
<211> LENGTH: 1063
<212> TYPE: DNA
<213> ORGANISM: Escherichia coli

<400> SEQUENCE: 45

| | | | | | |
|---|---|---|---|---|---|
| atggaaagcc | ctactccaca | gcctgctcct | ggttcggcga | ccttcatgga | aggatgcaaa | 60 |
| gacagtttac | cgattgttat | tagttatatt | ccggtggcct | ttgcgttcgg | tctgaatgcg | 120 |
| acccgtctgg | gattctctcc | tctcgaaagc | gttttttttct | cctgcatcat | ttatgcaggc | 180 |
| gcgagccagt | tcgtcattac | cgcgatgctg | cagccggga | gtagtttgtg | gattgctgca | 240 |
| ctgaccgtca | tggcaatgga | tgttcgccat | gtgttgtatg | gcccgtcact | gcgtagccgt | 300 |
| attattcagc | gtctgcaaaa | atcgaaaacc | gccctgtggg | cgtttggcct | gacggatgag | 360 |
| gttttttgccg | ccgcaaccgc | aaaactggta | cgcaataatc | gccgctggag | cgagaactgg | 420 |
| atgatcggca | ttgccttcag | ttcatggtca | tcgtgggtat | ttggtacggt | aataggggca | 480 |
| ttctccggca | gcggcttgct | gcaaggttat | cccgccgttg | aagctgcatt | aggttttatg | 540 |
| cttccggcac | tctttatgag | tttcctgctc | gcctctttcc | agcgcaaaca | atctctttgc | 600 |
| gttaccgcag | cgttagttgg | tgcccttgca | ggcgtaacgc | tattttctat | tcccgtcgcc | 660 |
| attctggcag | gcattgtctg | tggctgcctc | actgcgttaa | tccaggcatt | ctggcaagga | 720 |
| gcgcccgatg | agctatgagg | ttctgctgct | tgggttacta | gttggcgtgg | cgaattattg | 780 |
| cttccgctat | ttgccgctgc | gcctgcgtgt | gggtaatgcc | cgcccaacca | aacgtggcgc | 840 |
| ggtaggtatt | ttgctcgaca | ccattggcat | cgcctcgata | tgcgctctgc | tggttgtctc | 900 |
| taccgcacca | gaagtgatgc | acgatacacg | ccgtttcgtg | cccacgctgg | tcggcttcgc | 960 |
| ggtactgggt | gccagtttct | ataaaacacg | cagcattatc | atcccaacac | tgcttagtgc | 1020 |
| gctggcctat | gggctcgcct | ggaaagtgat | ggcgattata | taa | | 1063 |

<210> SEQ ID NO 46
<211> LENGTH: 495
<212> TYPE: DNA
<213> ORGANISM: Escherichia coli

<400> SEQUENCE: 46

| | | | | | |
|---|---|---|---|---|---|
| atggtagata | gcaagaagcg | ccctggcaaa | gatctcgacc | gtatcgatcg | taacattctt | 60 |
| aatgagttgc | aaaaggatgg | gcgtatttct | aacgtcgagc | tttctaaacg | tgtgggactt | 120 |
| tccccaacgc | cgtgccttga | gcgtgtgcgt | cggctggaaa | gacaagggtt | tattcagggc | 180 |
| tatacggcgc | tgcttaaccc | ccattatctg | gatgcatcac | ttctggtatt | cgttgagatt | 240 |
| actctgaatc | gtggcgcacc | ggatgtgttt | gaacaattca | ataccgctgt | acaaaaactt | 300 |
| gaagaaattc | aggagtgtca | tttagtatcc | ggtgatttcg | actacctgtt | gaaaacacgc | 360 |
| gtgccggata | tgtcagccta | ccgtaagttg | ctgggggaaa | ccctgctgcg | tctgcctggc | 420 |
| gtcaatgaca | cacggacata | cgttgttatg | gaagaagtca | agcagagtaa | tcgtctggtt | 480 |
| attaagacgc | gctaa | | | | | 495 |